(12) United States Patent
Cundiff et al.

(10) Patent No.: US 11,622,802 B2
(45) Date of Patent: Apr. 11, 2023

(54) ORTHOPEDIC IMPLANT ASSEMBLIES AND DEVICES

(71) Applicant: Fusion Orthopedics, LLC, Mesa, AZ (US)

(72) Inventors: Adam J. Cundiff, Gilbert, AZ (US); Nathan G. Peterson, Gilbert, AZ (US)

( * ) Notice: Subject to any disclaimer, the term of this patent is extended or adjusted under 35 U.S.C. 154(b) by 549 days.

(21) Appl. No.: 16/696,894

(22) Filed: Nov. 26, 2019

(65) Prior Publication Data

US 2020/0093528 A1 Mar. 26, 2020

Related U.S. Application Data

(63) Continuation-in-part of application No. 16/510,799, filed on Jul. 12, 2019, now Pat. No. 10,898,248, which is a continuation-in-part of application No. 15/663,173, filed on Jul. 28, 2017, now abandoned.

(51) Int. Cl.
| | |
|---|---|
| *A61B 17/86* | (2006.01) |
| *A61B 17/84* | (2006.01) |
| *A61B 17/68* | (2006.01) |
| *A61F 2/30* | (2006.01) |

(52) U.S. Cl.
CPC ........ *A61B 17/8605* (2013.01); *A61B 17/686* (2013.01); *A61B 17/846* (2013.01); *A61B 17/8685* (2013.01); *A61F 2/30* (2013.01); *A61B 2017/8655* (2013.01); *A61F 2002/30622* (2013.01)

(58) Field of Classification Search
CPC combination set(s) only.
See application file for complete search history.

(56) References Cited

U.S. PATENT DOCUMENTS

| | | | |
|---|---|---|---|
| 8,303,589 B2 | 11/2012 | Tyber | |
| 8,313,487 B2 | 11/2012 | Tyber | |
| 8,328,806 B2 | 12/2012 | Tyber | |
| 8,343,199 B2 | 1/2013 | Tyber | |
| 8,900,274 B2 | 12/2014 | Tyber | |
| 8,920,453 B2 | 12/2014 | Tyber | |
| 8,920,476 B2 | 12/2014 | Tyber | |
| 9,017,329 B2 | 4/2015 | Tyber | |
| 9,044,282 B2 | 6/2015 | Tyber | |
| 9,289,220 B2 | 3/2016 | Tyber | |
| 9,364,271 B2 | 6/2016 | Tyber | |
| 9,615,870 B2 | 4/2017 | Tyber | |
| 2010/0121325 A1 | 5/2010 | Tyber | |
| 2010/0256639 A1* | 10/2010 | Tyber | A61B 17/1775 606/62 |
| 2011/0125153 A1 | 5/2011 | Tyber | |
| 2011/0230884 A1 | 9/2011 | Tyber | |
| 2015/0173811 A1 | 6/2015 | Tyber | |
| 2016/0278823 A1 | 9/2016 | Tyber | |

* cited by examiner

*Primary Examiner* — Sameh R Boles

(57) ABSTRACT

Innovative orthopedic implant assemblies, devices, and methods are provided. One example assembly includes two implant devices. An example implant device includes two ends oppositely located with a bulbous portion located at one end and a screw portion located at the opposite end. An example second implant device includes two ends oppositely located with a looped portion defining an aperture located at one end and a nail portion located at the opposite end. The nail portion can include a tip and a smooth or substantially smooth portion. The second implant device can be implanted into a bone by striking the looped portion to facilitate the tip and at least part of the nail portion penetrating the bone.

16 Claims, 23 Drawing Sheets

ORTHOPEDIC IMPLANT ASSEMBLIES AND DEVICES

REFERENCE TO RELATED APPLICATIONS

This application is a Continuation-In-Part of and claims priority to U.S. patent application Ser. No. 16/510,799 filed on Jul. 12, 2019, which is a Continuation-In-Part of U.S. patent application Ser. No. 15/663,173 filed on Jul. 28, 2017, the contents of each application is incorporated herein by reference in their entirety.

BACKGROUND

Field of the Technology

The present technology relates generally to systems and apparatus for fusing bones and joints, and more particularly to, orthopedic implant assemblies and devices.

Description of the Related Art

Intraosseous fixation differs from traditional fixation devices in that hardware is not typically left exposed to soft tissue. As a newer form of fixation in, for example foot and ankle arthrodesis surgery, previous implant assemblies and/or devices require precise instrumentation that can be difficult to use. If an implant assembly/device and its associated instrumentation are not properly aligned, it can be difficult to produce desirable results. For instance, intra-operative problems can occur when bone fragments, soft tissue, and imposing tendons create improper alignment both for an implant assembly/device itself and from the implant assembly/device to instrumentation, which can lead to a lack of compression, weak compression, and/or complete misalignment. These problems can be exacerbated through patient non-compliance, movement, and/or osteoporotic bone quality, etc., each of can result in a disengagement of a proper fitment of the implant assembly/device. Further, soft tissue aggravation and/or non-unions often occur as components in an implant assembly disengage and implant device(s) constructs become loose rather than tight. Accordingly, previous implant assemblies and implant devices are not as efficient and/or reliable as they otherwise could be.

SUMMARY

Various embodiments provide innovative orthopedic implant methods, assemblies, and devices. An example method includes providing a first implant device including a first end and a second end oppositely located along a longitudinal first axis, a looped portion including an interior surface with a single groove disposed therein defining a first terminal axis at the first end, the looped portion defining an aperture, and a first threaded portion that extends along the longitudinal first axis and defining a second terminal axis at the second end. The method further includes providing a second implant device including a third end and a fourth end oppositely located along a longitudinal second axis, a bulbous portion that extends along the longitudinal second axis and defines a third terminal axis at the third end, the bulbous portion comprising a single thread disposed on an exterior surface of the bulbous portion, and a second threaded portion that extends along the longitudinal second axis and defines a fourth terminal axis at the fourth end. Further, the method includes facilitating locking the first implant device and the second implant device, locking the first implant device and the second implant device, or both facilitating locking the first implant device and the second implant device and locking the first implant device and the second implant device.

Another method includes providing a first implant device including a first end and a second end oppositely located along a longitudinal first axis, a looped portion including an aperture and defining a first terminal axis at the first end, and a nail portion that extends along the longitudinal first axis and defining a second terminal axis at the second end. The method further includes providing a second implant device including a third end and a fourth end oppositely located along a longitudinal second axis, a bulbous portion that extends along the longitudinal second axis and defines a third terminal axis at the third end, and a threaded portion that extends along the longitudinal second axis and defines a fourth terminal axis at the fourth end. Further, the method includes facilitating locking the first implant device and the second implant device, locking the first implant device and the second implant device, and both facilitating locking the first implant device and the second implant device and locking the first implant device and the second implant device.

A further method includes providing an implant device including a first end and a second end oppositely located along a longitudinal first axis, a looped portion including an aperture and defining a first terminal axis at the first end, and a nail portion that extends along the longitudinal first axis and defining a second terminal axis at the second end. The method further includes implanting the implant device into a portion of bone via the nail portion.

BRIEF DESCRIPTION OF THE DRAWINGS

The present disclosure is illustrated by way of example, and not by way of limitation, in the figures of the accompanying drawings in which like reference numerals are used to refer to similar elements.

DETAILED DESCRIPTION OF THE DRAWINGS

Figure 1A:
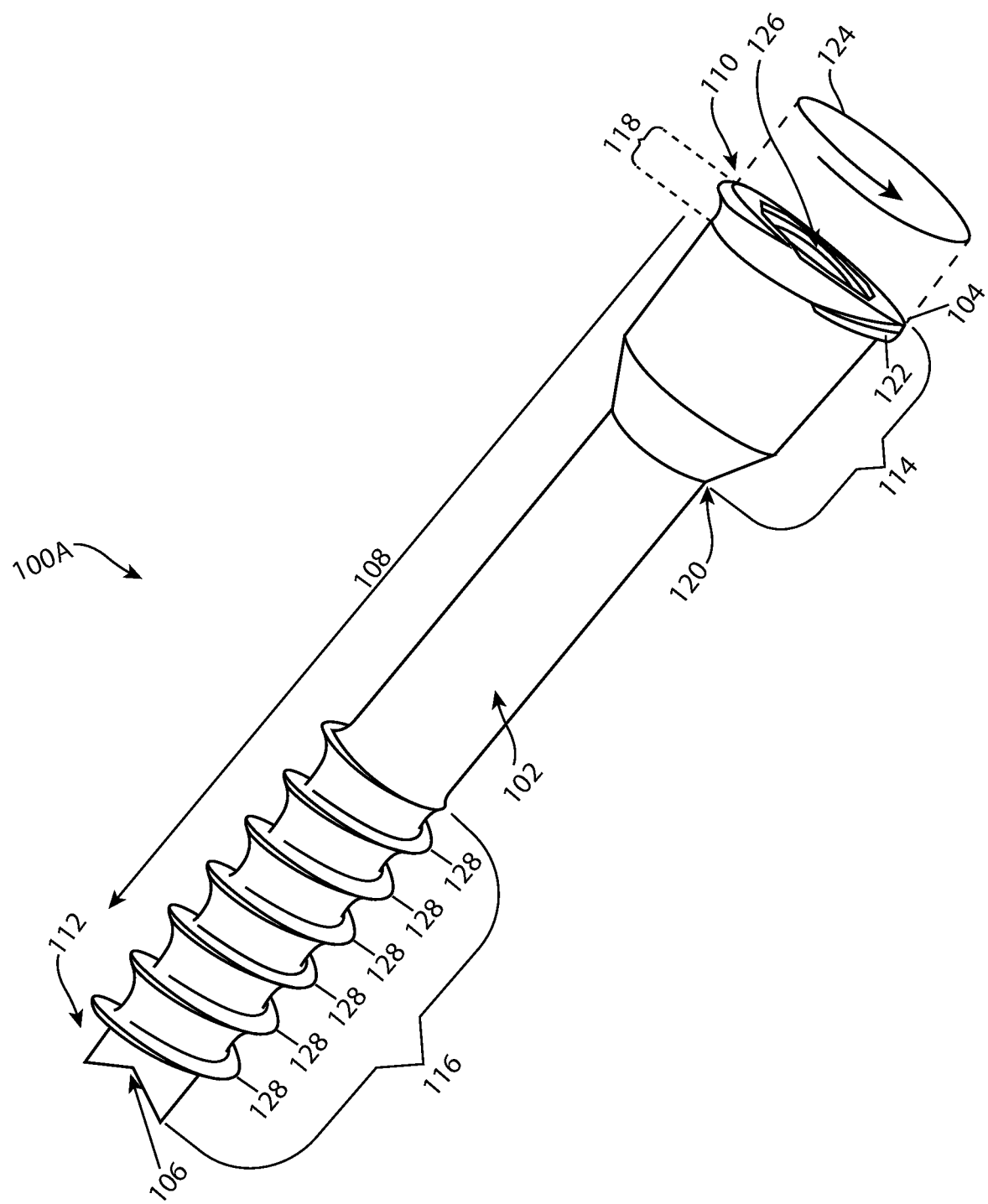
FIGS. 1A through 1C are diagrams illustrating various embodiments of an implant device.

The innovative technology disclosed herein includes various aspects, such as orthopedic implant devices, assemblies, and methods for fusing bones and joints. The disclosed technology provides is advantageously more efficient and/or more reliable than previous implant devices and/or assemblies. It should be understood that language used in the present disclosure has been principally selected for readability and instructional purposes, and not to limit the scope of the subject matter disclosed herein.

Various embodiments may provide a locking feature that can ensure proper fitment to reduce implant impedance and/or poor surgical outcomes regardless of an implant environment. Some implant devices may utilize a Morse-taper fitment along with an interference thread on a crown that can aid instruments and interfacing screws in aligning and properly implanting of assemblies and devices. An interference thread can allow instruments to lock in conjunction with the taper to further ensure that an assembly/implant is properly aligned. Furthermore, the interference thread may aid in locking the screw compression in place and reducing the chance of an implant device from backing out over time.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Further, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The schematic flowchart diagrams and/or schematic block diagrams in the Figures illustrate the architecture, functionality, and operation of possible implementations. It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Although various arrow types and line types may be employed in the flowchart and/or block diagrams, they are understood not to limit the scope of the corresponding embodiments. Indeed, some arrows or other connectors may be used to indicate only an exemplary logical flow of the depicted embodiment.

The description of elements in each figure below may refer to elements of proceeding figures. For instance, like numbers can refer to similar elements in all figures, including alternate embodiments of similar elements.

With reference now to the figures, FIG. 1A is a diagram illustrating an example implant device 100A in accordance with various embodiments. Implant device 100A may include a shaft portion 102 with a first end 104 and a second end 106 that are opposite one another along a longitudinal axis 108 and define a first terminal axis 110 and a second terminal axis 112, respectively. As shown, the implant device 100A may comprise, among other features, a bulbous portion 114 at the first end 104 and a screw portion 116 at the second end 106. Although the various embodiments may be referred to herein as an implant device 100A, at least some embodiments of the implant device 100A may be considered and/or referred to as a lag screw.

The bulbous portion 114, in various embodiments, may originate at the first terminal axis 110 and extend along the longitudinal axis 108 and terminate at any position on the shaft portion 102. As such, the bulbous portion 114 may include any suitable height or length. The bulbous portion 114, in some embodiments, may include a height or length that allows the bulbous portion 114 to engage a looped portion of another implant device (e.g., looped portion 214 of implant device 200A, 200B, and 200C in FIGS. 2A, 2B, and 2C, respectively) to lock implant device 100A to the other implant device, as discussed elsewhere herein (see e.g., FIGS. 3A and/or 3B).

In various embodiments, the looped portion 214 may include any suitable shape that is capable of being engaged with the looped portion of another implant device (e.g., the looped portion 214). In other words, the bulbous portion 114 can include any shape that complements and/or corresponds to the looped portion of the other implant device. Non-limiting examples of a shape suitable for the bulbous portion 114 may include, but are not limited to, a circle, an oval, and/or any other circular shape, etc., among other example shapes.

Alternatively, or additionally, the shape of the bulbous portion 114 may, in various embodiments, include a suitable amount of tapering. In some embodiments, the tapering may originate at a crown 118 of the bulbous portion 114 that is located beginning at the first terminal axis 110 and continually taper down along the longitudinal axis 108 to a foot 120 of the bulbous portion 114. In further embodiments, the tapering may originate at the crown 118 and terminate a position that is away from the foot 120 or the tapering may originate at a position that is away from the crown 118 and continually taper down along the longitudinal axis 108 to the foot 120 such that the bulbous portion 114 can include a tapered portion and a non-tapered portion. In alternative embodiments, the tapering may originate at a position that is away from the crown 118 and terminate at a position that is away from the foot 120 such that the bulbous portion 114 can include a tapered portion and multiple non-tapered portions.

In various embodiments, a tapered portion of the bulbous portion 114 may include any suitable type of tapering that is known or developed in the future and is capable of creating a force or compression, in any desired amount, when engaged and/or connected with another implant device (e.g., implant device 200A, 200B, and 200C in FIGS. 2A, 2B, and 2C, respectively), as discussed elsewhere herein. In some embodiments, the taper in the bulbous portion 114 may comprise a Morse-taper.

A bulbous portion 114 may include a thread 122 located on its external surface that rotates in a helix along a rotational axis 124 of the bulbous portion 114 and down the longitudinal axis 108. The thread 122, in various embodiments, may rotate in the range of about ten degrees (10°) to three hundred sixty degrees (360°), among other examples. In some embodiments, the thread 122 may rotate 360° along the rotational axis 124. In further embodiments, the thread 122 may rotate less than 360° along the rotational axis 124. In an example embodiment, the thread 122 rotates ninety degrees (90°) along the rotational axis 124. Various embodiments of the thread 122 can be considered a single thread since they rotate less than or equal to 360° along the rotational axis 124.

In various embodiments, the thread 122 may rotate at any suitable angle along the rotational axis 124. In some embodiments, the thread 122 may rotate at an angle to create a spaced apart or wide thread along the longitudinal axis 108, while in other embodiments the thread 122 may rotate at an angle to create a tight or narrow thread along the longitudinal axis 108. In further embodiments, the thread 122 can rotate at the same angle and/or an angle that corresponds to an angle at which a groove on an interior surface of a looped portion (e.g., groove 222 on looped portion 214) rotates such that the thread 122 and the groove lock the bulbous portion 114 and the looped portion together when engaged, as discussed elsewhere herein (e.g., FIGS. 3A and/or 3B).

The thread 122 may include any suitable height and/or shape that can allow the thread 122 to engage a groove or other thread. In various embodiments, the thread 122 may include any suitable height and/or shape that may be compatible with and/or may correspond to a depth and/or shape of a groove (e.g., groove 222) that can allow the bulbous portion 114 to be locked with a looped portion (e.g., looped portion 214 in FIGS. 2A, 2B, and 2C) such that implant device 100A can form a portion of an implant assembly (e.g., implant assembly 300A in FIGS. 3A and/or 3B) along with at least one other implant device (e.g., implant device 200A, 200B, and 200C in FIGS. 2A, 2B, and 2C, respectively), as discussed elsewhere herein (e.g., FIGS. 3A and/or 3B).

In further embodiments, the thread 122 may include a sufficient amount of height such that the thread 122 can be considered a wing. In some embodiments, the thread 122 may include a height in the range of about 0.5 mm to about 2 mm, although other heights are possible and contemplated herein.

Further, the thread 122 can originate and/or terminate at any suitable location on the bulbous portion 114. In various embodiments, the thread 122 may originate at a position along the crown 118 of the bulbous portion 114, may terminate at a position along the foot 120 of the bulbous portion 114, may originate at a position along the crown 118 and terminate at a position along the foot 120, or may originate at a position that is away from the crown 118 and terminate at a position that is away from the foot 120.

The bulbous portion 114, in some embodiments, may include one or more additional threads 122 such that the bulbous portion 114 can include multiple single-threads. For instance, the threads 122 may be spaced apart such that no single thread 122 includes greater than 360° of rotation along the rotational axis 124. In some aspects, two or more single-threads 122 may may rotate in parallel or not in parallel in relation to one another. In further aspects, two or more single-threads 122 may originate at the same location (e.g., crown 118) or different locations on the bulbous portion 114 and/or terminate at the same location (e.g., foot 120) or different locations on the bulbous portion 114. For instance, two or more threads 122 may originate at the crown 118 of the bulbous portion 114, one thread 122 may originate at the crown 118 and a second thread 122 may terminate at the foot 120 of the bulbous portion, two or more threads 122 may terminate at the foot 120, two or more threads 122 may originate at the crown 118 and terminate at the foot 120, or two or more threads 122 may both originate and terminate at different locations on the bulbous portion 114, etc., among other location combinations that are possible and contemplated herein.

Figure 2A:
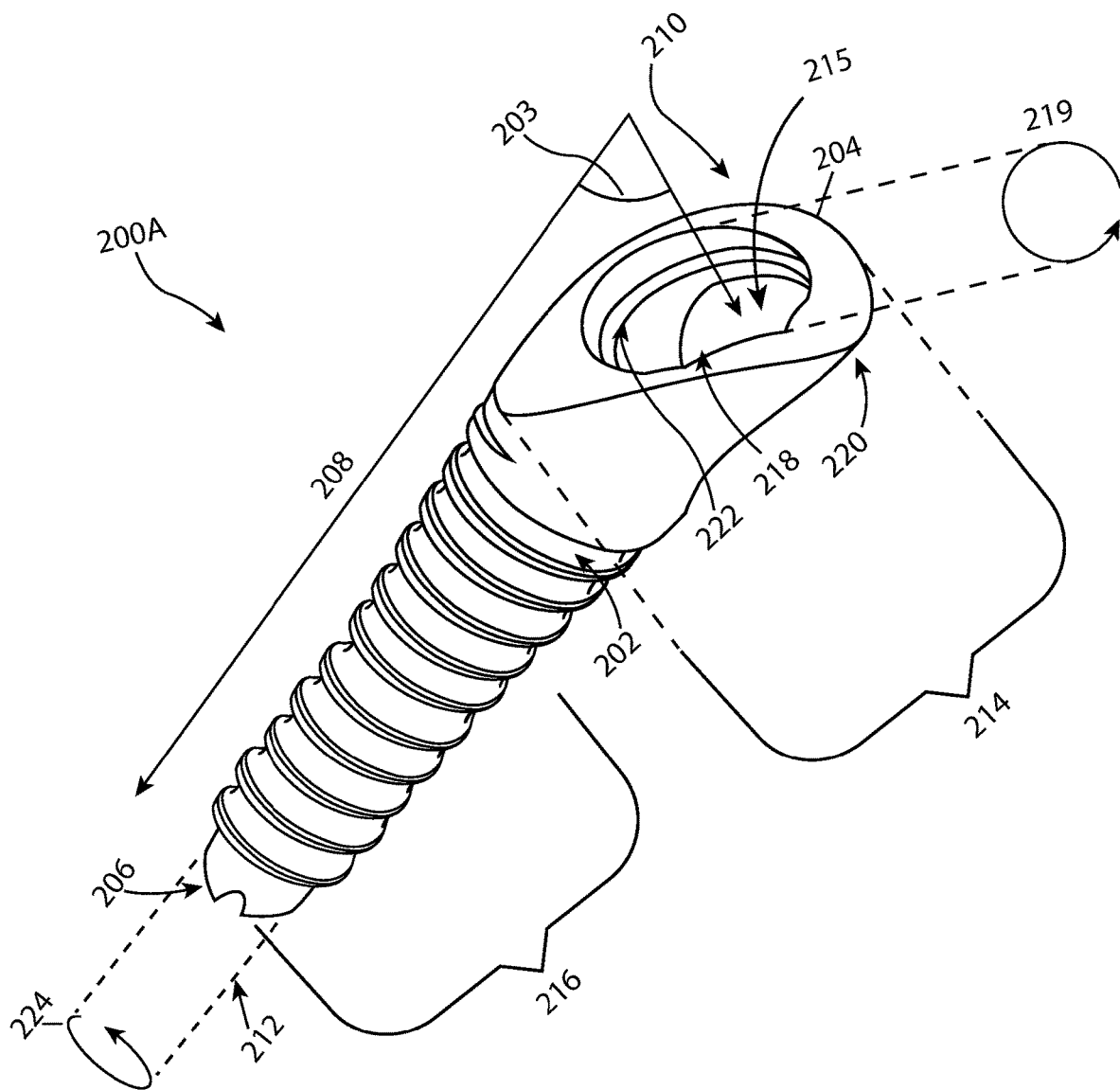
FIGS. 2A through 2G are diagrams illustrating various embodiments of another implant device that can be engaged with the implant devices of FIGS. 1A through 1C to create the various implant assemblies of FIGS. 3A through 3H.
Figure 2B:
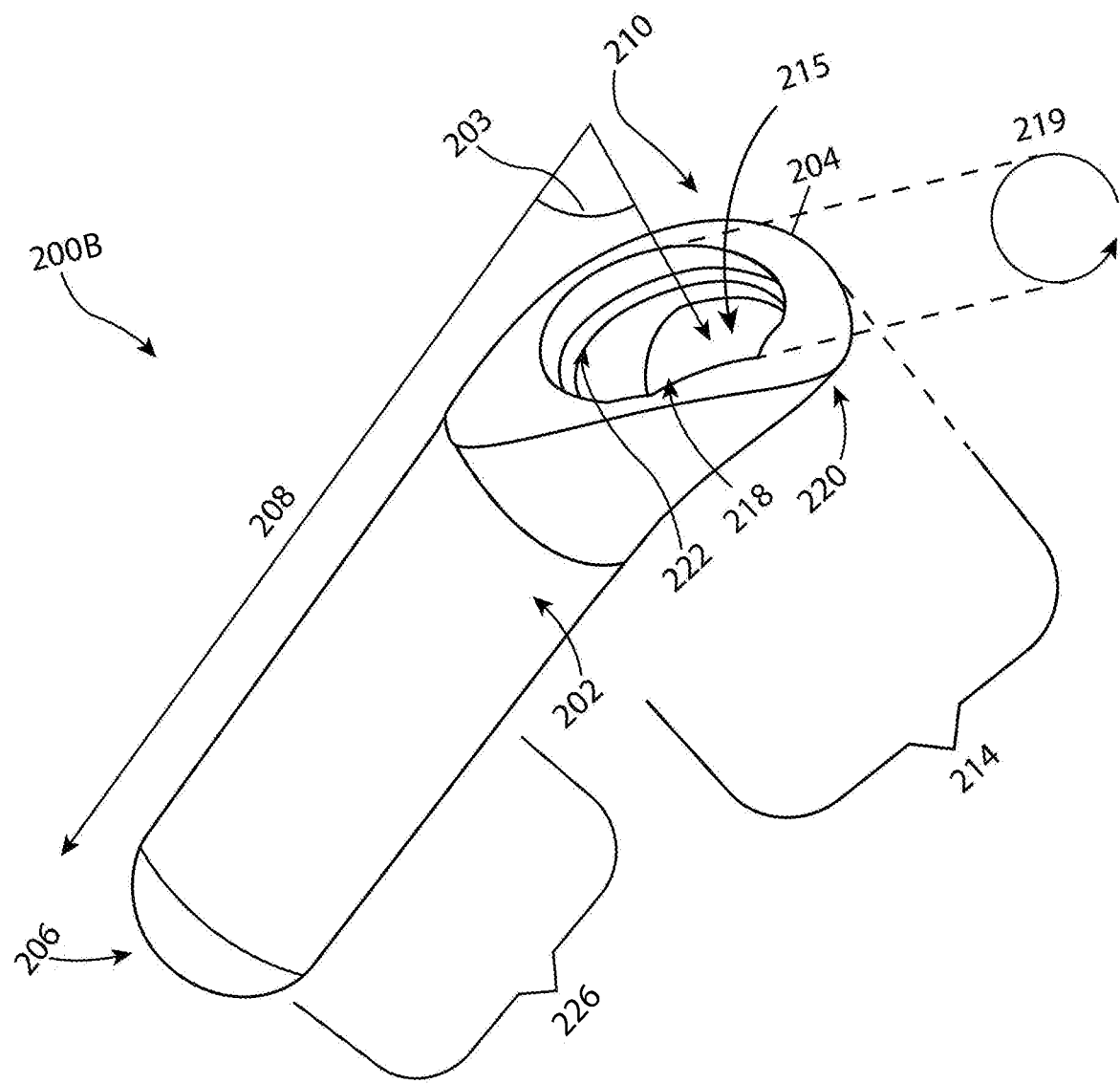
Figure 2C:
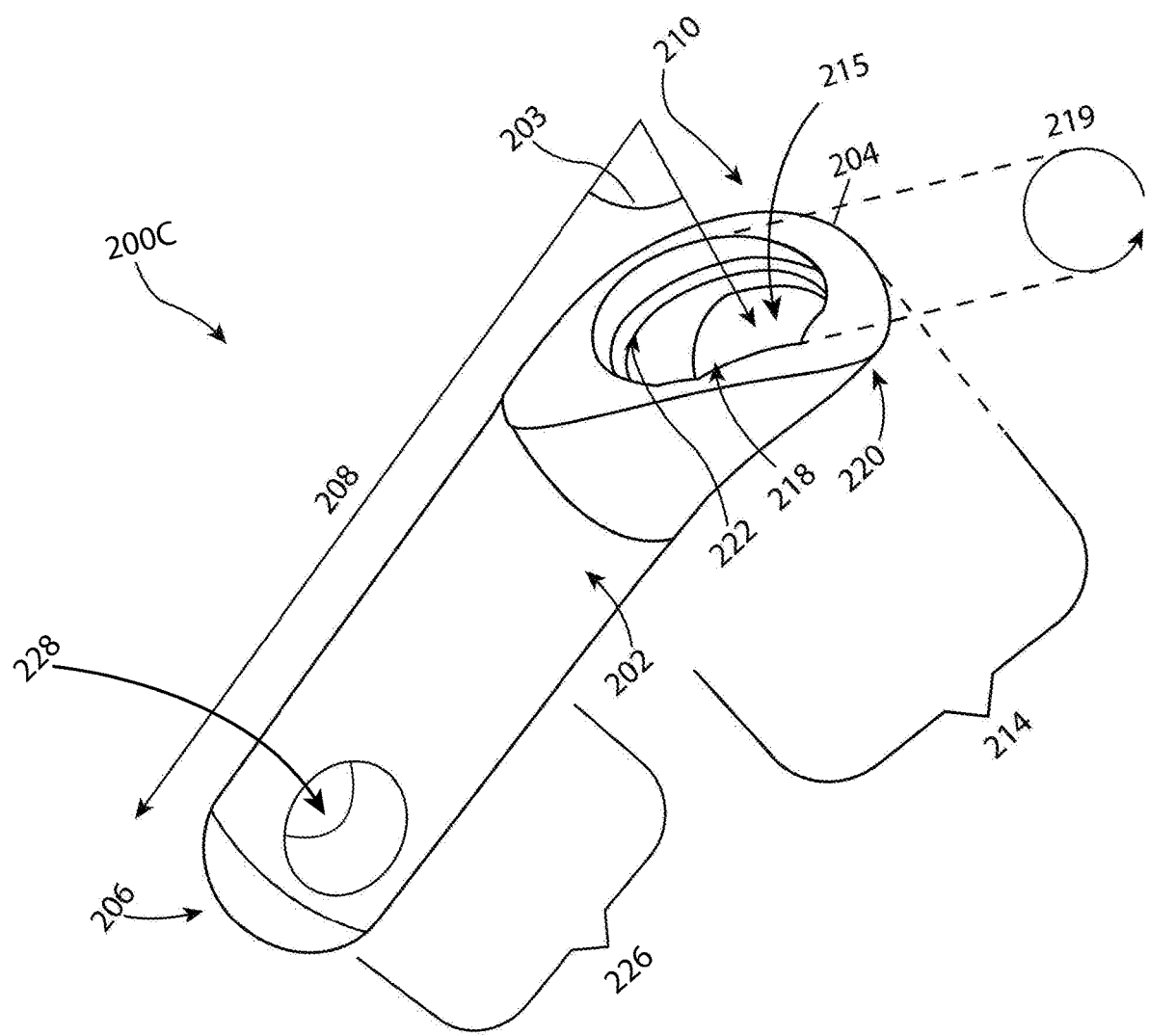

The crown 118 of the bulbous portion 114, in various embodiments, may include a mechanism 126 that can be engaged by a tool that allows the implant device 100A to be implanted into a bone or joint and/or engaged with a looped portion of another implant device (e.g., looped portion 214 of implant device 200A, 200B, and 200C in FIGS. 2A, 2B, and 2C, respectively). In some embodiments, the mechanism 126 may include characteristics similar to an aperture in the head of a screw (e.g., a Phillips screw, flat-head screw, star screw, box screw, hex screw, etc., among other examples) that can allow a screwdriver, Allen wrench, hex key, rotational tool, or similar tool, etc. to engage the aperture 126.

The second end 106, in various embodiments, may include a screw portion 116 on the shaft portion 102 that extends along the longitudinal axis 108 and terminates at the second terminal axis 112. The screw portion 116 may be any suitable length that allows the implant device 100A to be implanted into a bone or joint. Further, the screw portion 116 may be tapered in any suitable manner that is known or developed in the future that is capable of allowing the implant device 100A to be implanted into a bone or joint. The screw portion 116 may further include a plurality of threads 128 including any suitable height, any suitable width, and/or suitable amount of space between each thread 128. For instance, the plurality of threads 128 may include any suitable number rotations or suitable amount of rotation along the rotational axis 124 that is greater than 360°.

The implant device 100A may comprise any material that is known or developed in the future that is capable of being implanted into a bone or joint. Non-limiting examples of suitable materials include, but are not limited to, a metal, an alloy, a composite material, and/or the like materials, etc., among other example materials. Some suitable specific non-limiting examples include titanium, stainless steel, nitinol, cobalt chromium, and/or aluminum, etc., among other suitable materials that are possible and contemplated herein.

In various embodiments, the implant device 100A may include any suitable shape that is capable of being implanted into a bone or joint. Non-limiting examples of a shape suitable for the implant device may include, but are not limited to, a circle, an oval, and/or any other circular shape, etc., among other example shapes.

Further, the implant device 100A may include any suitable length and/or suitable circumference that can allow the implant device 100A to be implanted into a bone or joint. A non-limiting example range of lengths includes, but is not limited to, about 10 mm to about 150 mm. Further, a non-limiting example range of circumferences includes, but is not limited to, about 2 mm to about 100 mm.

Figure 1B:
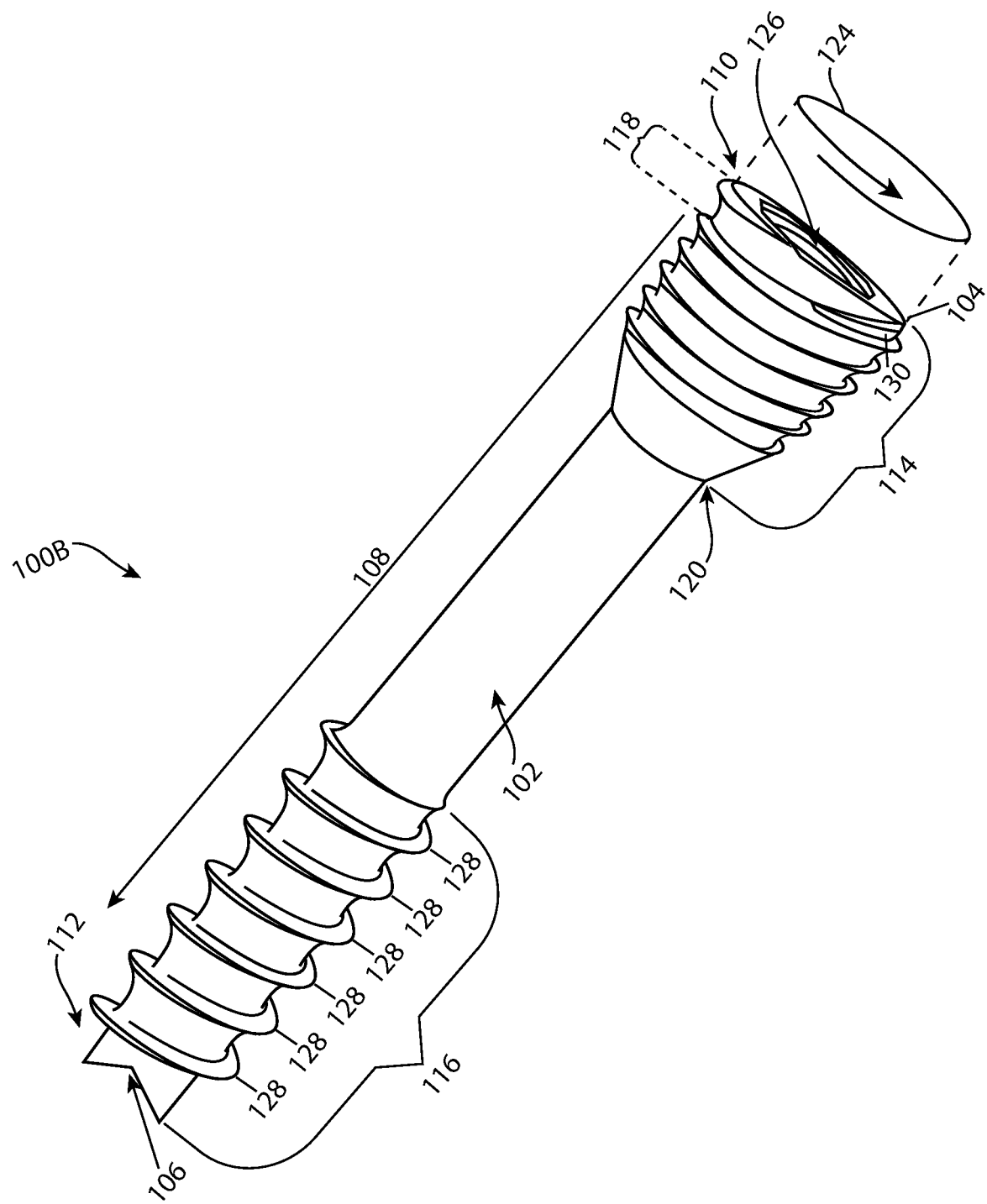

Referring now to FIG. 1B, FIG. 1B is a diagram illustrating another example implant device 100B in accordance with various embodiments. Implant device 100B may include a shaft portion 102, a first end 104, a second end 106, a horizontal axis 108, a first terminal axis 110, a second terminal axis 112, a bulbous portion 114, a screw portion 116, a crown 118, a foot 120, a rotational axis 124, a mechanism 126, and threads 128 similar to the implant device 100A discussed above. Implant device 100B may further include, among other components, a plurality of threads 130 on the external surface of bulbous portion 114. That is, one difference between implant device 100A and implant device 100B is that the bulbous portion 114 in implant device 100A includes a single thread 122, while the bulbous portion 114 in implant device 100B includes multiple threads 130.

The threads 130 may be located on the external surface of bulbous portion 114 and rotate in a helix along the rotational axis 124 of the bulbous portion 114 and down the longitudinal axis 108. The threads 130, in various embodiments, may rotate at any suitable angle along the rotational axis 124. In some embodiments, the threads 130 may rotate at an angle to create spaced apart or widely spaced threads 130 along the longitudinal axis 108, while in other embodiments the threads 130 may rotate at an angle to create tight or narrowly spaced threads along the longitudinal axis 108. In further embodiments, the threads 130 can rotate at the same angle and/or an angle that corresponds to an angle at which a groove on an interior surface of a looped portion (e.g., groove 222 or grooves 230 on looped portion 214) rotates such that the threads 130 and the groove 222 or grooves 230 lock the bulbous portion 114 and the looped portion 214 together when engaged, as discussed elsewhere herein.

The threads 130 may include any suitable height and/or shape that can allow the threads 130 to engage a groove 222 or grooves 230 or other thread. In various embodiments, the threads 130 may include any suitable height and/or shape that may be compatible with and/or may correspond to a depth and/or shape of a groove (e.g., groove 222), grooves (e.g., grooves 230) and/or otherwise (e.g., a smooth area 232) that can allow the bulbous portion 114 to be locked with a looped portion (e.g., looped portion 214 in FIGS. 2B through 2G) such that implant device 100B can form a portion of an implant assembly (e.g., implant assembly 300C through 300H in FIGS. 3C through 3H) along with at least one other implant device (e.g., implant device 200B through 200G in FIGS. 2B through 2G, respectively), as discussed elsewhere herein (e.g., FIG. 3C through 3H).

In further embodiments, the threads 130 may include any suitable height. In some embodiments, the threads 130 may include a height in the range of about 0.1 mm to about 2 mm, although other heights are possible and contemplated herein.

Further, the threads 130 can originate and/or terminate at any suitable location on the bulbous portion 114. In various embodiments, the threads 130 may originate at a position along the crown 118 of the bulbous portion 114, may terminate at a position along the foot 120 of the bulbous portion 114, may originate at a position along the crown 118 and terminate at a position along the foot 120, or may originate at a position that is away from the crown 118 and terminate at a position that is away from the foot 120.

Figure 1C:
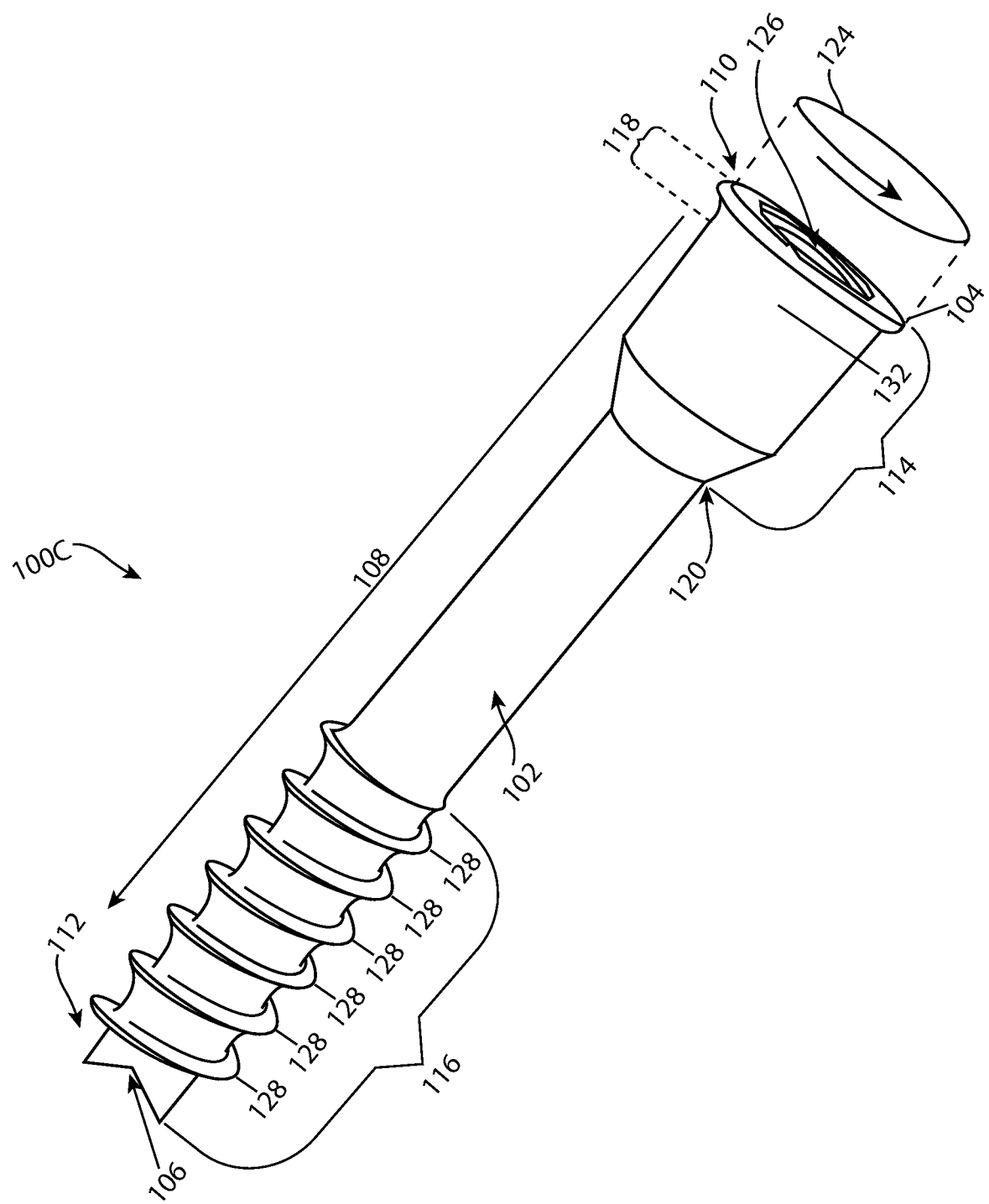

With reference to FIG. 1C, FIG. 1C is a diagram illustrating another example implant device 100C in accordance with various embodiments. Implant device 100C may include a shaft portion 102, a first end 104, a second end 106, a horizontal axis 108, a first terminal axis 110, a second terminal axis 112, a bulbous portion 114, a screw portion 116, a crown 118, a foot 120, a rotational axis 124, a mechanism 126, and threads 128 similar to the implant devices 100A and 100B discussed above. Implant device 100C may further include, among other components, substantially smooth (e.g., textured, non-threaded, and/or thread-less, etc.) or smooth (e.g., non-threaded, thread-less, etc.) exterior surface 132 (or substantially smooth or smooth area 132) on the bulbous portion 114. That is, one difference between implant devices 100A/100B and implant device 100C is that the bulbous portion 114 in implant device 100C does not include a groove 122 or grooves 130. Instead, the bulbous portion 114 on implant device 100C includes a substantially smooth (e.g., a textured, non-threaded, etc.) or smooth external surface 132 (e.g., a smooth or substantially smooth area).

Referring now to FIG. 2A, FIG. 2A is a diagram illustrating an example implant device 200A in accordance with various embodiments. Implant device 200A may include a shaft portion 202 with a first end 204 and a second end 206 that are opposite one another along a longitudinal axis 208 and define a first terminal axis 210 and a second terminal axis 212, respectively. As shown, the implant device 200A may comprise, among other features, a looped portion 214 defining an aperture 215 at the first end 204 and a screw portion 216 at the second end 206. Although the various embodiments may be referred to herein as an implant device 200A, at least some embodiments of the implant device 200A may be considered and/or referred to as a post screw.

The looped portion 214, in various embodiments, may originate at the first terminal axis 210 and extend along the longitudinal axis 208 and terminate at any position on the shaft portion 202. As such, the looped portion 214 may include any suitable height or circumference. The looped portion 214, in some embodiments, may include a height or circumference that allows the looped portion 214 to engage a bulbous portion of another implant device (e.g., bulbous portion 114 of implant device 100A) to lock implant device 200A to the other implant device, as discussed elsewhere herein (e.g., FIGS. 3A and/or 3B).

In various embodiments, the looped portion 214 may include any suitable shape that allows the bulbous portion of another implant device (e.g., bulbous portion 114) to be inserted through the aperture 215. In other words, the looped portion 214 can include any shape such that the aperture 215 complements and/or corresponds to the bulbous portion of the other implant device. Non-limiting examples of a shape suitable for the looped portion 214 may include, but are not limited to, a circle, an oval, and/or any other circular shape, etc., among other example shapes.

Alternatively, or additionally, the shape of the looped portion 214 may, in various embodiments, include a suitable amount of tapering on an interior surface that defines the aperture 215. In some embodiments, the tapering may originate at an insertion side 218 of the looped portion 214/aperture 215 that is located along a rotational axis 219. In further embodiments, the tapering may originate at the insertion side 218 and terminate at a position that is away from the exit side 220 or the tapering may originate at a position that is away from the insertion side 218 and continually taper down to the exit side 220 such that the interior surface can include a tapered portion and a non-tapered portion. In alternative embodiments, the tapering may originate at a position that is away from the insertions side 218 and terminate at a position that is away from the exit side 220 such that the interior surface of the looped portion 214 can include a tapered portion and multiple non-tapered portions.

In various embodiments, the interior surface of the looped portion 214 may be compatible with and/or correspond to any suitable type of tapering that is known or developed in the future and is capable of creating a force or compression, in any desired amount, when engaged and/or connected with a bulbous portion of another implant device (e.g., bulbous portion 114), as discussed elsewhere herein. In some embodiments, the interior surface of the looped portion 214 may be compatible with and/or correspond to a bulbous portion comprising a Morse-taper.

The aperture 215 may be created at an angle 203 with respect to the longitudinal axis 208 of the implant device 200A. The angle 203, in various embodiments, can be any suitable and/or desired angle in the range of about thirty degrees (30°) to about one hundred fifty degrees (150°), although other angles and/or ranges are possible and contemplated herein. In some embodiments, the angle 203 may be in the range of about 62 degrees (62°) to about 68 degrees (68°), among other example angles and/or ranges. In one embodiment, the angle 203 may be about sixty-five degrees (65°), among other possible angles that are contemplated herein.

The looped portion 214 may include a groove 222, which can also be considered a thread, which is located on its interior surface that is proximate to the aperture 215 and rotates in a helix along the rotational axis 219. The groove 222, in various embodiments, may rotate in the range of about ten 10° to 360°, among other examples. In some embodiments, the groove 222 may rotate 360° along the rotational axis 219. In further embodiments, the groove 222 may rotate less than 360° along the rotational axis 219. In an example embodiment, the groove 222 rotates 90° along the rotational axis 219. Various embodiments of the groove 222 can be considered a single-groove since they rotate less than or equal to 360° along the rotational axis 219.

In various embodiments, the groove 222 may rotate at any suitable angle along the rotational axis 219. In some embodiments, the groove 222 may rotate at an angle to create a spaced apart or wide groove, while in other embodiments the groove 222 may rotate at an angle to create a tight or narrow groove. In further embodiments, the groove 222 can rotate at the same angle and/or an angle that corresponds to an angle at which a thread on a bulbous portion (e.g., thread 122 on bulbous portion 114) rotates such that the groove 222 and the thread lock the bulbous portion and the looped portion 214 together when engaged, as discussed elsewhere herein (e.g., FIGS. 3A through 3D).

The groove 222 may include any suitable depth and/or shape that can allow the groove 222 to engage a thread. In various embodiments, the groove 222 may include any suitable depth and/or shape that may be compatible with and/or may correspond to a height and/or shape of a thread (e.g., thread 122) that can allow the looped portion 214 to be locked with a bulbous portion (e.g., bulbous portion 114) such that implant device 200A can form a portion of an implant assembly (e.g., implant assembly 300A in FIGS. 3A and/or 3B) along with at least one other implant device (e.g., implant device 100A), as discussed elsewhere herein (e.g., FIGS. 3A and/or 3B). In some embodiments, the groove 222 may include a depth in the range of about 0.05 mm to about 6 mm, although other depths are possible and contemplated herein.

Further, the groove 222 can originate and/or terminate at any suitable location on the interior surface of the looped portion 214. In various embodiments, the groove 222 may originate at a position along the insertion side 218 of the looped portion 214, may terminate at a position along the exit side 220 of the looped portion 214, may originate at a position along the insertion side 218 and terminate at a position along the exit side 220, or may originate at a position that is away from the insertion side 218 and terminate at a position that is away from the exit side 220.

In some embodiments, the looped portion 214 may include one or more grooves 222 that can provide a self-correction mechanism when a single thread (e.g., thread 122) engages the looped portion 214. For instance, the groove(s) 222 may be angled and/or positioned in a manner such that the insertion angle and/or trajectory of an implant device (e.g., implant device 100A) into the aperture 215 can be automatically or a least semi-automatically modified as a thread (e.g., thread 122) of the implant device catches or engages a particular groove 222 to better ensure that the implant device is properly implanted and/or implanted on a proper angle/trajectory.

In some embodiments, the looped portion 214 may include one or more additional grooves 222 such that the looped portion 214 can provide multiple engagement points for a single thread (e.g., thread 122). For instance, the grooves 222 may be spaced apart such that a single thread has multiple locations or opportunities to catch or engage a groove 222. In some aspects, two or more single-grooves 222 may rotate in parallel or not in parallel in relation to one another. In further aspects, two or more single-grooves 222 may originate at different locations on the same rotational plane, different locations on different rotational planes, or the same location on different rotational planes, etc., among other examples that may provide multiple opportunities or chances for a single thread (e.g., thread 122) to engage a groove 222 on the interior surface of the looped portion 214. The one or more additional grooves 222 in conjunction with the single-groove 222 that may provide multiple engagement points for a single thread (e.g., thread 122), in some embodiments, can further provide a self-correction mechanism for inserting an implant device (e.g., implant device 100A), as discussed elsewhere herein.

The looped portion 214, in further embodiments, may include one or more additional grooves 222 such that the looped portion 214 can accommodate multiple single-threads (e.g., single-threads 122). For instance, the grooves 222 may be spaced apart such that no single-groove 222 includes greater than 360° of rotation along the rotational axis 219. In some aspects, two or more single-grooves 222 may rotate in parallel or not in parallel in relation to one another. In further aspects, two or more single-grooves 222 may originate at the same location (e.g., a point of the looped portion 214 on/near the insertion side 218 or at an intermediary point between the insertion side and the exit side 220) or different locations on the looped portion 214 and/or terminate at the same location (e.g., a point of the looped portion 214 on/near the exit side 220 or at an intermediary point between the insertion side and the exit side 220) or different locations on the looped portion 214. For instance, two or more grooves 222 may originate at the insertion side 218 of the looped portion 214, one groove 222 may originate at the insertion side 218 and a second groove 222 may terminate at the exit side 220 of the looped portion 214, two or more grooves 222 may terminate at the exit side 220, two or more grooves 222 may originate at the insertion side 218 and terminate at the exit side 220, or two or more grooves 222 may both originate and terminate at different locations on the looped portion 214, etc., among other location combinations that are possible and contemplated herein. The one or more additional grooves 222 in conjunction with the single-groove 222 that can accommodate multiple single-threads (e.g., single-threads 122), in some embodiments, can further provide a self-correction mechanism for inserting an implant device (e.g., implant device 100A), as discussed elsewhere herein.

The second end 206, in various embodiments, may include a screw portion 216 on the shaft portion 102 that rotates around a rotational axis 224 and extends along the longitudinal axis 208 and terminates at the second terminal axis 212. The screw portion 216 may be any suitable length that allows the implant device 200A to be implanted into a bone or joint. Further, the screw portion 216 may be tapered in any suitable manner that is known or developed in the future that is capable of allowing the implant device 200A to be implanted into a bone or joint. The screw portion 216 may further include a plurality of threads including any suitable height, any suitable width, and/or suitable amount of space between each thread. For instance, the plurality of threads may include any suitable number rotations or suitable amount of rotation along the rotational axis 224 that is greater than 360°.

The implant device 200A may comprise any material that is known or developed in the future that is capable of being implanted into a bone or joint. Non-limiting examples of suitable materials include, but are not limited to, a metal (e.g., aluminum), an alloy, a composite material, and/or the like materials, etc., among other example materials. Some suitable specific non-limiting examples include titanium, stainless steel, nitinol, cobalt chromium, and/or aluminum, etc., among other suitable materials that are possible and contemplated herein.

In various embodiments, the implant device 200A may include any suitable shape that is capable of being implanted into a bone or joint. Non-limiting examples of a shape suitable for the implant device may include, but are not limited to, a circle, an oval, and/or any other circular shape, etc., among other example shapes.

Further, the implant device 200A may include any suitable length and/or suitable circumference that can allow the implant device 200A to be implanted into a bone or joint. A non-limiting example range of lengths includes, but is not limited to, about 5 mm to about 150 mm. Further, a non-limiting example range of circumferences includes, but is not limited to, about 4 mm to about 50 mm.

With reference to FIG. 2B, FIG. 2B is a diagram illustrating an example implant device 200B in accordance with various embodiments. Implant device 200B may include a shaft portion 202 with a first end 204 including a looped portion 214 defining an aperture 215 and further including a second end 206 similar to the implant device 200A, as discussed elsewhere herein. As shown, the implant device 200B may further comprise, among other features, a smooth, substantially smooth, or nail portion 226 at the second end 206. The nail portion 226 is smooth or substantially smooth in that the nail portion 226 does include the threaded portion 216 of the implant device 200A. The nail portion 226 may include any suitable tip and/or construction (e.g., sharp, pointed, rounded, etc.) that allows the implant device 200B to be tapped, struck, driven, hammered, nailed, pounded, and/or otherwise similarly inserted into and/or attached to a bone. Although the various embodiments may be referred to herein as an implant device 200B, at least some embodiments of the implant device 200B may be considered and/or referred to as a post screw.

The looped portion 214 with the single groove 222, in some embodiments, is configured to house and/or accommodate an implant device 100 that includes a bulbous portion 114 that includes a single groove 122. In additional or alternative embodiments, the looped portion 214 with the single groove 222 is configured to house and/or accommodate an implant device 100 that includes a bulbous portion 114 that includes a plurality of grooves 130, a substantially smooth exterior surface 132, and/or a smooth exterior surface 132.

Referring to FIG. 2C, FIG. 2C is a diagram illustrating an example implant device 200C in accordance with various embodiments. Implant device 200C may include a shaft portion 202 with a first end 204 including a looped portion 214 defining an aperture 215 and a second end 206 with a nail portion 226 similar to the implant device 200B, as discussed elsewhere herein. As shown, the implant device 200C may further comprise, among other features, an aperture 228 in the nail portion 226 at the second end 206.

The aperture 228 may include any suitable shape that can allow and/or enable the implant device 200C to be better secured into a bone. Similarly, the aperture 228 may include any suitable dimensions (e.g., length, width, volume, height, circumference, etc.) that can allow and/or enable the implant device 200C to be better secured into a bone. Although the various embodiments may be referred to herein as an implant device 200C, at least some embodiments of the implant device 200C may be considered and/or referred to as a post screw.

The looped portion 214 with the single groove 222, in some embodiments, is configured to house and/or accommodate an implant device 100 that includes a bulbous portion 114 that includes a single groove 122. In additional or alternative embodiments, the looped portion 214 with the single groove 222 is configured to house and/or accommodate an implant device 100 that includes a bulbous portion 114 that includes a plurality of grooves 130, a substantially smooth exterior surface 132, and/or a smooth exterior surface 132.

Figure 2D:
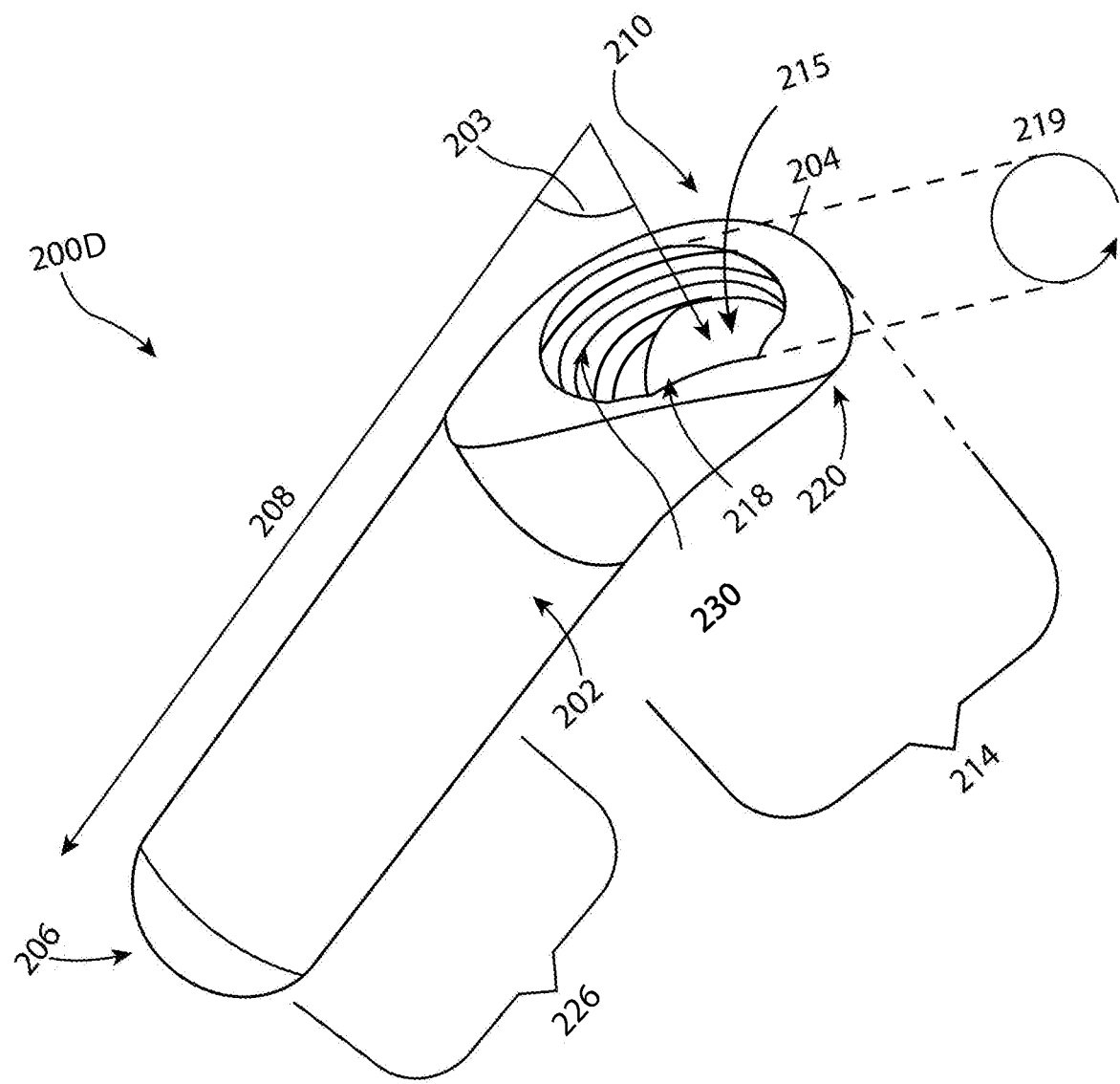

With reference to FIG. 2D, FIG. 2D is a diagram illustrating an example implant device 200D in accordance with various embodiments. Implant device 200D may include a shaft portion 202 with a first end 204 including a looped portion 214 defining an aperture 215 and further including a second end 206 similar to the implant device 200A and further comprises a smooth, substantially smooth, or nail portion 226 at the second end 206 similar to the implant device 200B, as discussed elsewhere herein.

In various embodiments, implant device 200D further comprises, among other components, a plurality of grooves 230 located on an interior surface of the looped portion 214. That is, while various embodiments of an implant device include a single groove 222 located on an interior surface of the looped portion 214, implant device 200D includes two or more grooves 230 located on an interior surface of the looped portion 214 that are similar to the single groove 222.

The quantity of grooves 230 located on an interior surface of the looped portion 214 may include any suitable quantity of grooves 230. In some embodiments, the quantity of grooves 230 corresponds to the quantity of threads 130 included on the bulbous portion 114 of an implant device 100B.

The looped portion 214 with the plurality of grooves 220, in some embodiments, is configured to house and/or accommodate an implant device 100 that includes a bulbous portion 114 that includes a single groove 122. In additional or alternative embodiments, the looped portion 214 with the plurality of grooves 230 is configured to house and/or accommodate an implant device 100 that includes a bulbous portion 114 that includes a plurality of grooves 130, a substantially smooth exterior surface 132, and/or a smooth exterior surface 132.

Figure 2E:
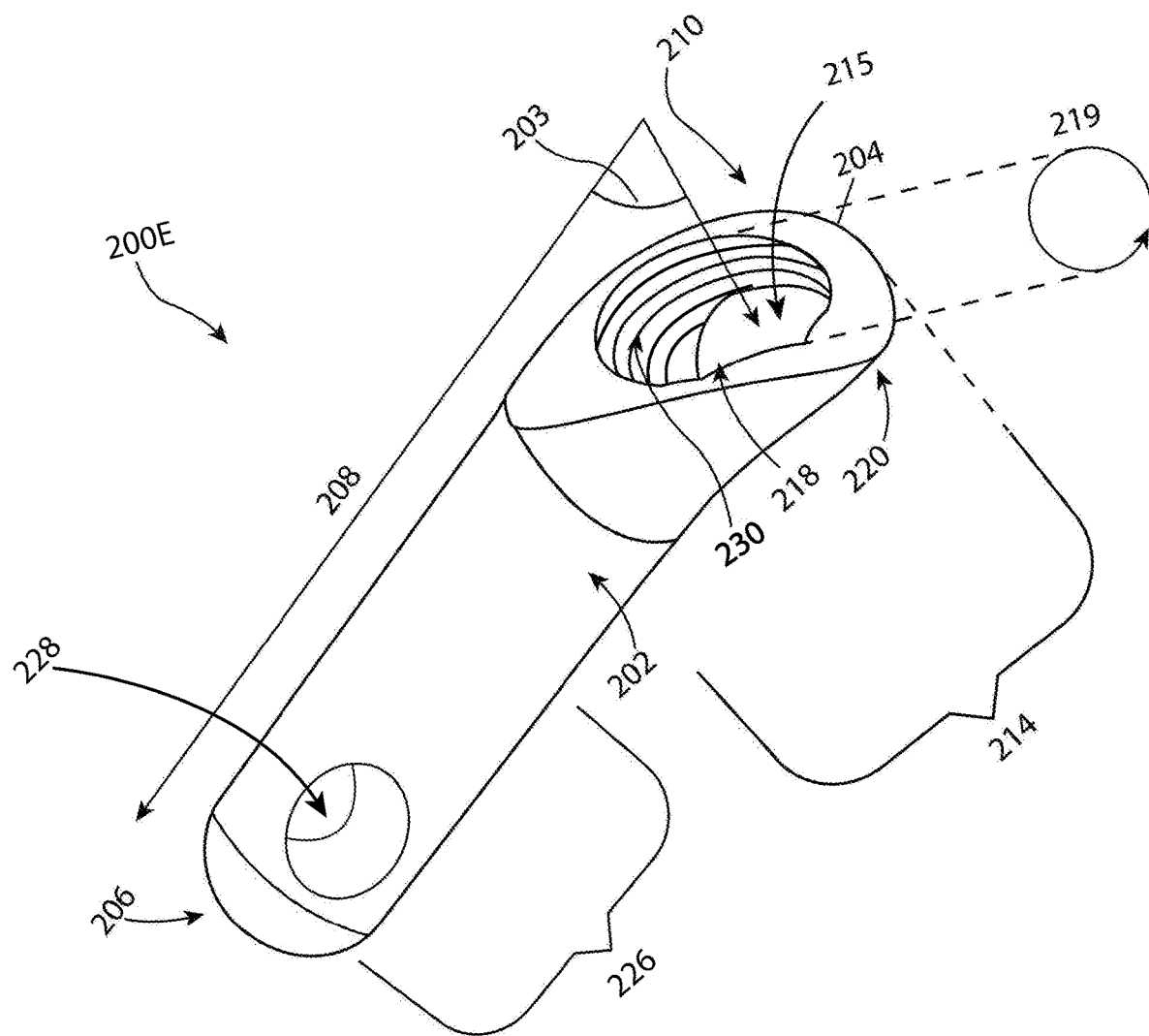

Referring to FIG. 2E, FIG. 2E is a diagram illustrating an example implant device 200C in accordance with various embodiments. Implant device 200E may include a shaft portion 202 with a first end 204 including a looped portion 214 defining an aperture 215 and a second end 206 with a nail portion 226 similar to the implant device 200B and an aperture 228 in the nail portion 226 at the second end 206 similar to the implant device 200C, as discussed elsewhere herein. In various embodiments, implant device 200E further includes, among other components, a plurality of grooves 230 located on an interior surface of the looped portion 214 similar to implant device 200D, as discussed elsewhere herein.

The looped portion 214 with the plurality of grooves 230, in some embodiments, is configured to house and/or accommodate an implant device 100 that includes a bulbous portion 114 that includes a single groove 122. In additional or alternative embodiments, the looped portion 214 with the plurality of grooves 230 is configured to house and/or accommodate an implant device 100 that includes a bulbous portion 114 that includes a plurality of grooves 130, a substantially smooth exterior surface 132, and/or a smooth exterior surface 132.

Figure 2F:
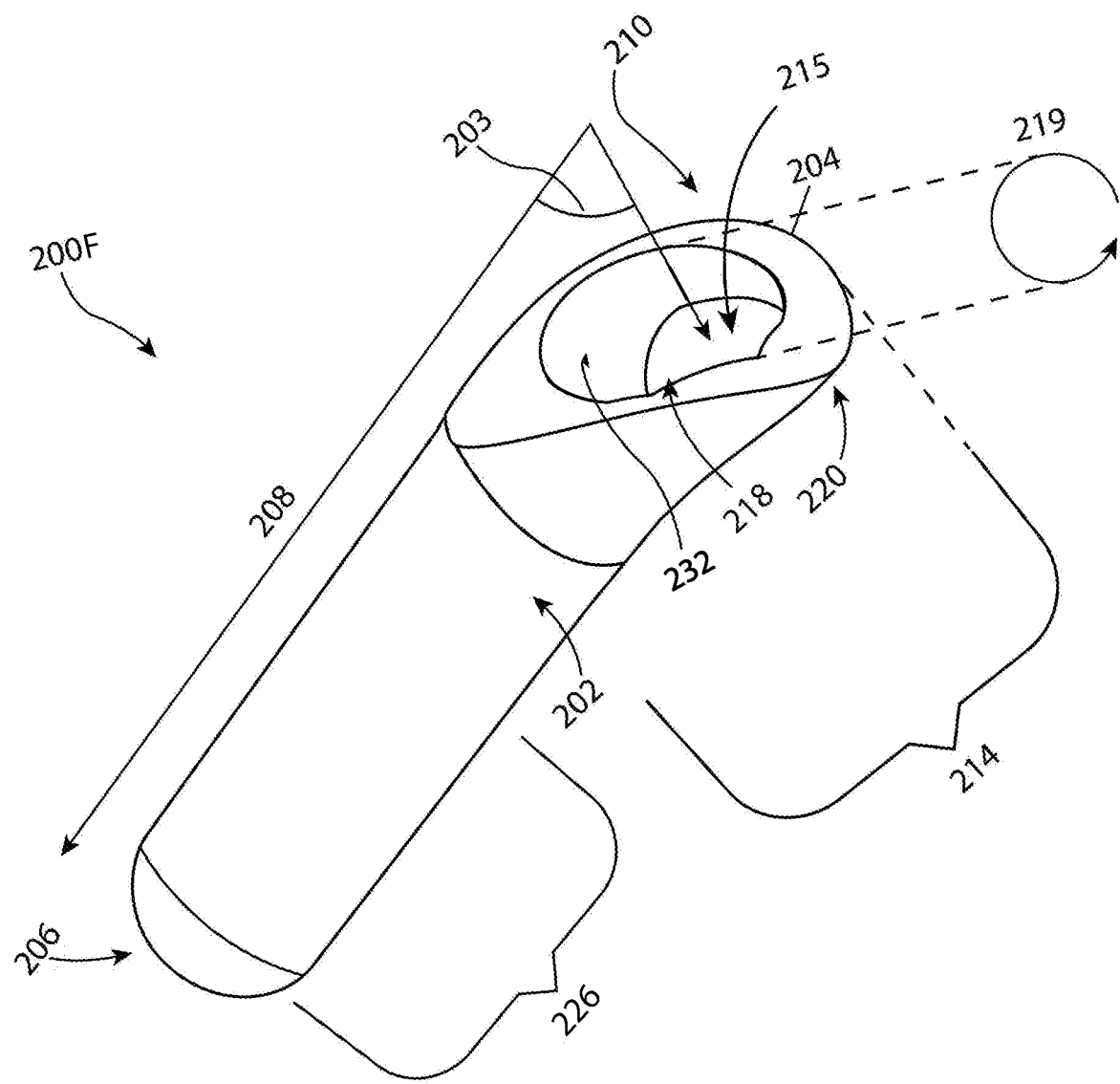

With reference to FIG. 2F, FIG. 2F is a diagram illustrating an example implant device 200F in accordance with various embodiments. Implant device 200F may include a shaft portion 202 with a first end 204 including a looped portion 214 defining an aperture 215 and further including a second end 206 similar to the implant device 200A and further comprises a smooth, substantially smooth, or nail portion 226 at the second end 206 similar to the implant device 200B, as discussed elsewhere herein. In various embodiments, implant device 200F further comprises, among other components, a substantially smooth (e.g., textured, non-grooved, and/or groove-less, etc.) or smooth (e.g., non-grooved, groove-less, etc.) interior surface 232 (or substantially smooth or smooth area 232) of the looped portion 214 that defines aperture 215.

The looped portion 214 with the smooth interior surface 232, in some embodiments, is configured to house and/or accommodate an implant device 100 that includes a bulbous portion 114 that includes a single groove 122. In additional or alternative embodiments, the looped portion 214 with the smooth interior surface 232 is configured to house and/or accommodate an implant device 100 that includes a bulbous portion 114 that includes a plurality of grooves 130, a substantially smooth exterior surface 132, and/or a smooth exterior surface 132.

Figure 2G:
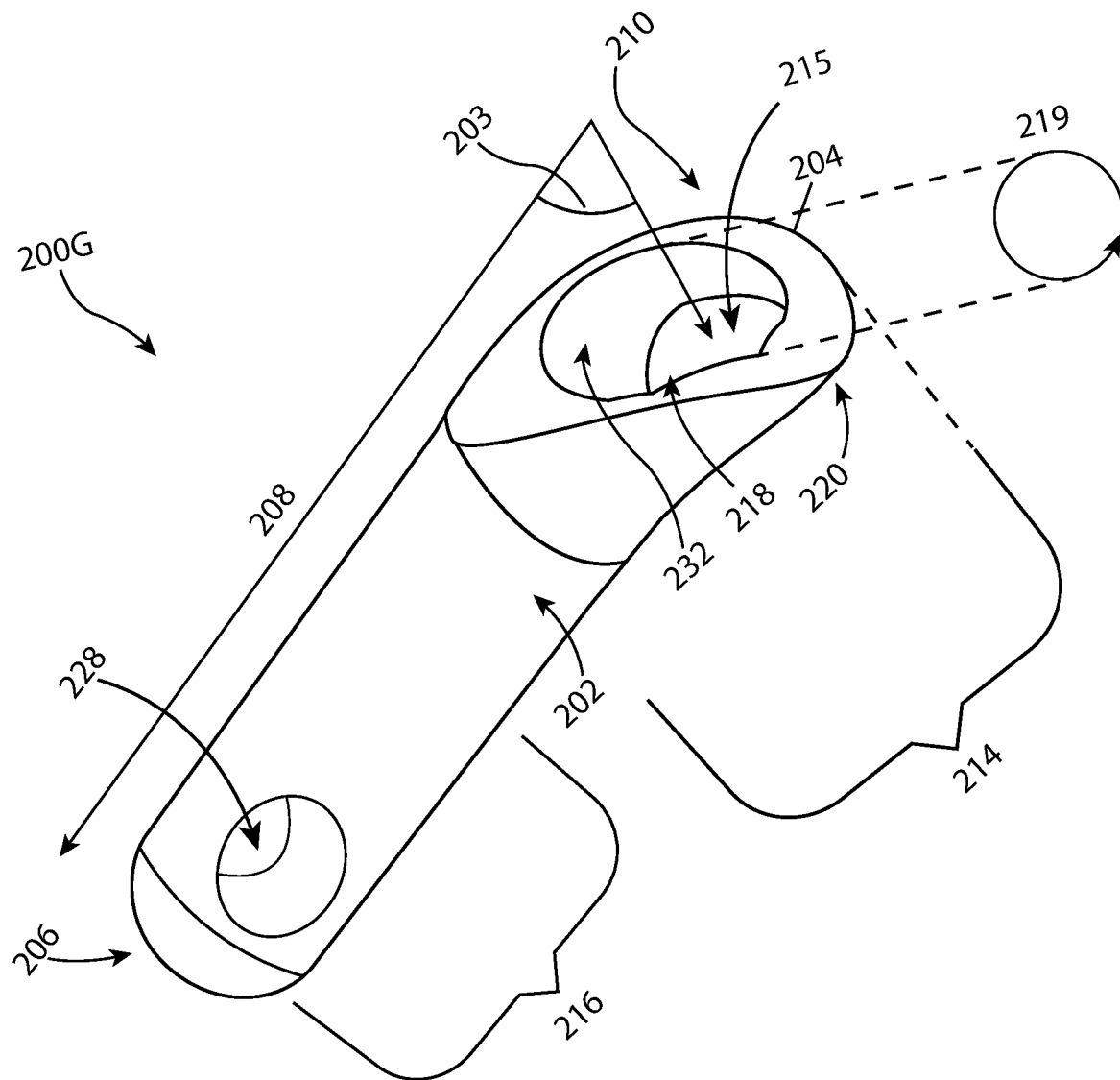

Referring to FIG. 2G, FIG. 2G is a diagram illustrating an example implant device 200C in accordance with various embodiments. Implant device 200G may include a shaft portion 202 with a first end 204 including a looped portion 214 defining an aperture 215 and a second end 206 with a nail portion 226 similar to the implant device 200B and an aperture 228 in the nail portion 226 at the second end 206 similar to the implant device 200C, as discussed elsewhere herein. In various embodiments, implant device 200G further includes, among other components, a looped portion 214 with a smooth interior surface 232 similar to implant device 200F, as discussed elsewhere herein.

The looped portion 214 with the smooth interior surface 232, in some embodiments, is configured to house and/or accommodate an implant device 100 that includes a bulbous portion 114 that includes a single groove 122. In additional or alternative embodiments, the looped portion 214 with the smooth interior surface 232 is configured to house and/or accommodate an implant device 100 that includes a bulbous portion 114 that includes a plurality of grooves 130, a substantially smooth exterior surface 132, and/or a smooth exterior surface 132.

Figure 3A:
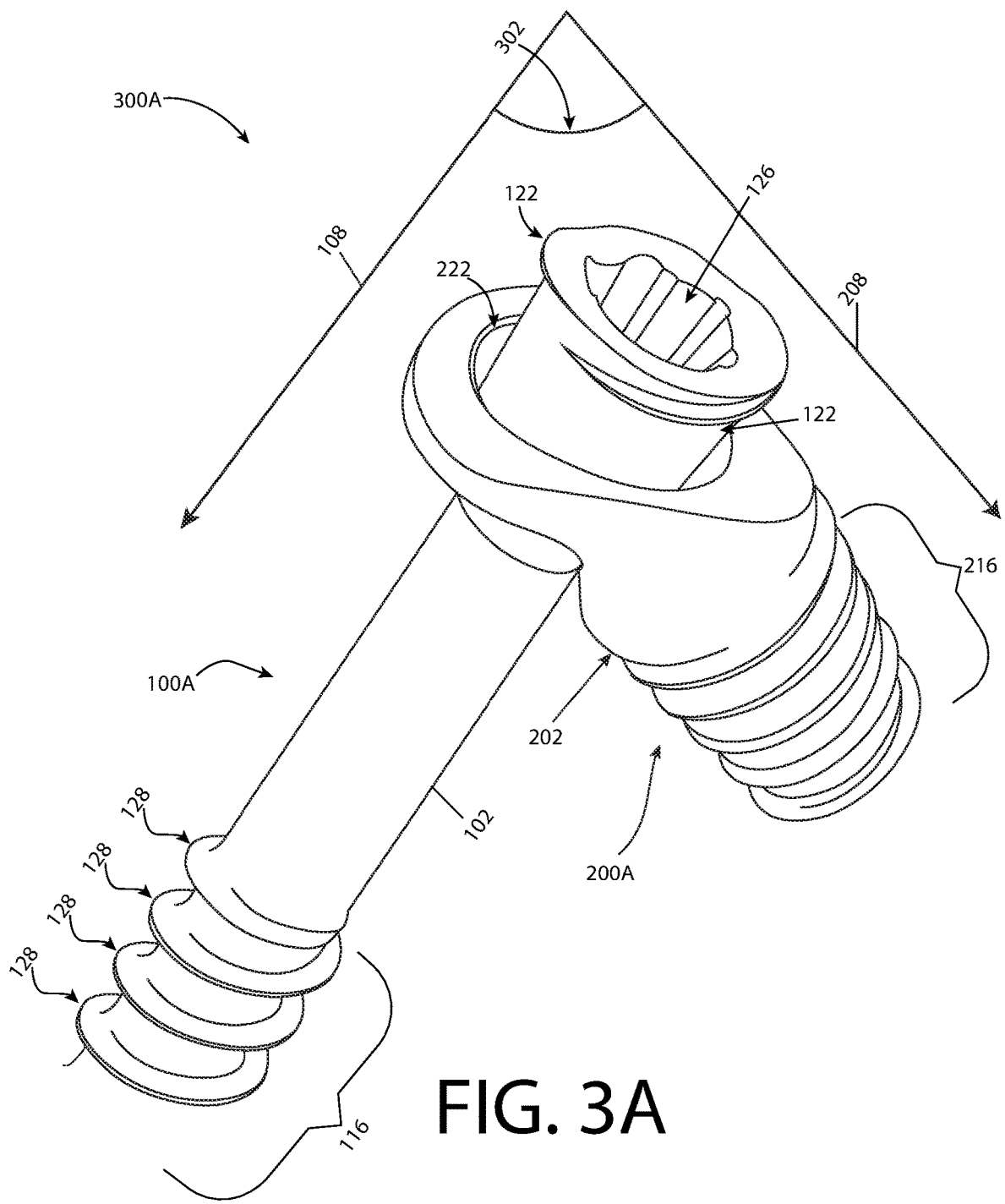
FIGS. 3A through 3H are diagrams illustrating various views of various examples of implant assemblies including an implant device of FIG. 1A, FIG. 1B, or FIG. 1C and an implant device of FIG. 2A, FIG. 2B, FIG. 2C, FIG. 2D, FIG. 2E, FIG. 2F, or FIG. 2G.
Figure 3B:
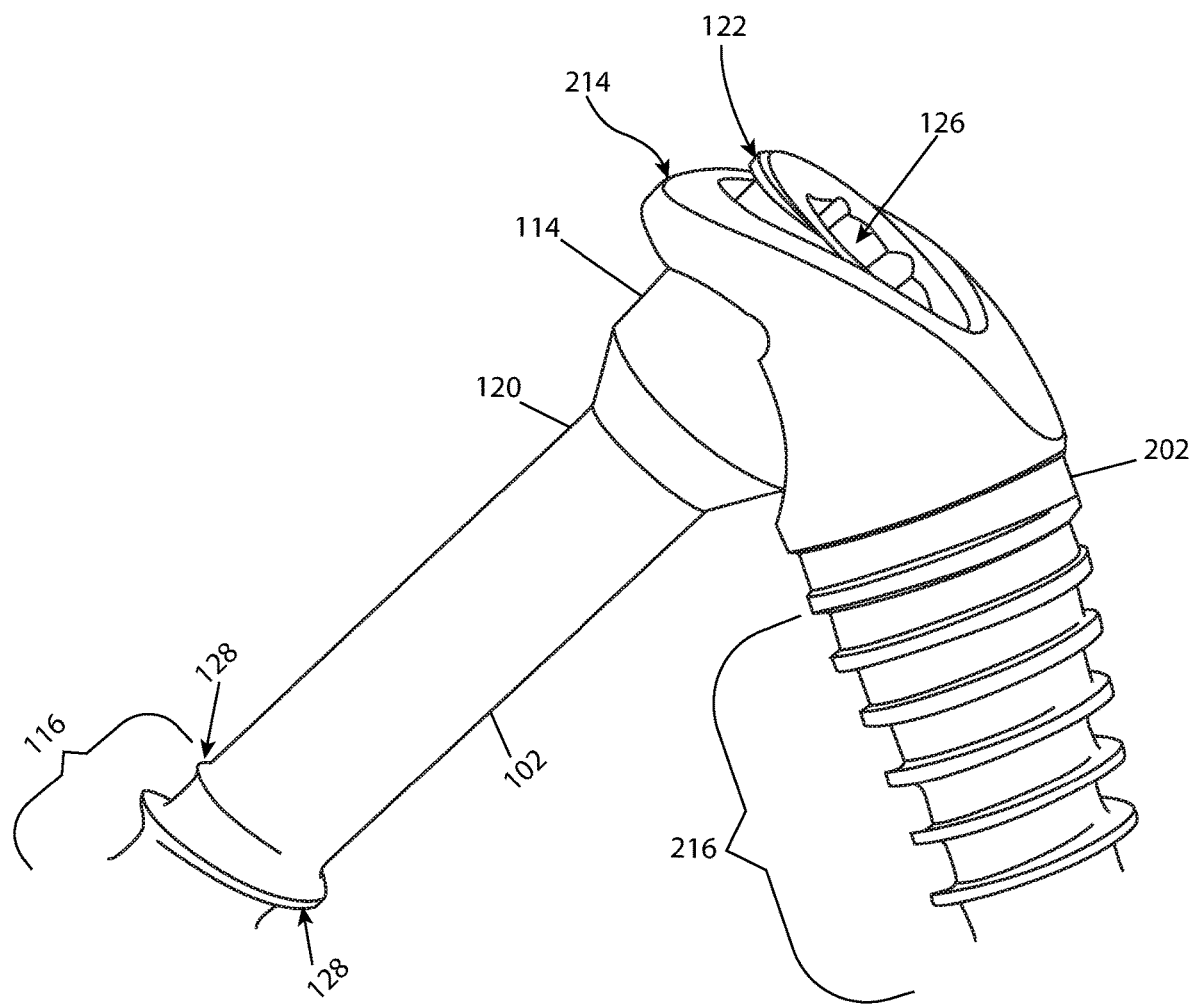

With reference now to FIGS. 3A and 3B, FIGS. 3A and 3B illustrate an anteroposterior view and a lateral view, respectively, of an example implant assembly 300A in accordance with various embodiments. As shown, implant assembly 300A can comprise implant device 100A and implant device 200A.

In some embodiments, implant device 100A and implant device 200A may comprise the same material. In further embodiments, implant device 100A and implant device 200A can comprise different materials.

In accordance with various embodiments of implant assembly 300A, the implant device 200A may be initially implanted into a bone or a joint during use. For instance, the screw portion 216 of the implant device 200A may be implanted or screwed into a bone or joint using an implant tool.

Further, the implant device 100A may subsequently be inserted through aperture 215, the screw portion 116 first, until the bulbous portion 214 is seated inside the aperture 215. Once seated within the aperture 215, the implant device 100A may be rotated by inserting an appropriate tool, as discussed elsewhere herein, inside the mechanism 126 and rotating or twisting the tool so that the thread 122 or threads 122 engage and couple to the groove 222 and/or grooves 222.

The implant device 100A may be rotated until the bulbous portion 114 is sufficiently coupled to the looped portion 214 of the implant device 214 and/or a last thread 128 in the plurality threads 128 of the screw portion 116 that is capable of engaging a bone/joint is engaged (e.g., is screwed into the bone/joint), the screw(s) 122 of the implant device 100A may be engaged with the grove(s) 222 of the implant device 200A to lock or couple implant devices 100A and 200A together. A last thread in the plurality threads 128 of the screw portion 116 that is capable of engaging a bone/joint may be the thread that is farthest from the second end 206 and/or the second terminal axis 212 of implant device 200A or may be any other thread in the plurality threads 128.

In various embodiments, implant devices 100A and 200A may be implanted or screwed into the same bone or joint, different bones or joints, or in a bone and a joint, as needed or desired. In some embodiments, a self-correcting mechanism in the looped portion 214, as discussed elsewhere herein, may assist in ensuring that the implant device 100A is inserted through aperture 215 and implanted or screwed into the bone or joint at the proper angle and/or trajectory.

An angle 302 may be created between the horizontal axis 108 of the implant device 100A and the horizontal axis 208 of the implant device 200A when the single-thread(s) 122 and the single-groove(s) 222 are engaged with one another. The angle 302, in various embodiments, can be any suitable and/or desired angle in the range of about 30° to about 150°, although other angles and/or ranges are possible and contemplated herein. In some embodiments, the angle 302 may be in the range of about 62° to about 68°, among other example angles and/or ranges. In one embodiment, the angle 302 may be about 65°, among other possible angles that are contemplated herein.

While the use of a standard thread-groove screw engagement has been described in various embodiments herein, a reverse thread-groove screw engagement may be possible and is contemplated herein for various embodiments. For instance, the single-thread(s) 122 in the implant device 100A and the single-groove(s) 222 in the implant device 200A, in some embodiments, may be reverse threaded and correspond to one another. In further embodiments, the plurality of threads 128 in the implant device 100A and/or the plurality of threads in the implant device 200A may be reverse threaded.

A single-thread/single-groove screw engagement utilizing, for example, a single thread 122 and a single-groove 222 can allow the implant devices 100A and 200A to be more easily engaged, locked, and/or coupled to one another, can allow the implant devices 100A and 200A to be more accurately engaged, locked, and/or coupled to one another, can be more efficient, can require less work, and/or can provide a stronger, more stable, and/or more secure locking connection than other technologies and/or techniques. Further, a single-thread/multi-groove engagement using, for example, a single thread 122 and multiple single-grooves 222 can provide similar benefits as a single-thread/single-groove engagement and may provide one or more added features and/or one or more further improvements. In addition, multi-single-thread/multi-single-groove engagements using, for example, multiple single-threads 122 and multiple single-grooves 222 can provide similar benefits as a single-thread/single-groove engagement and/or a single-thread/multi-groove engagement and may provide one or more added features and/or one or more further improvements.

Figure 3C:
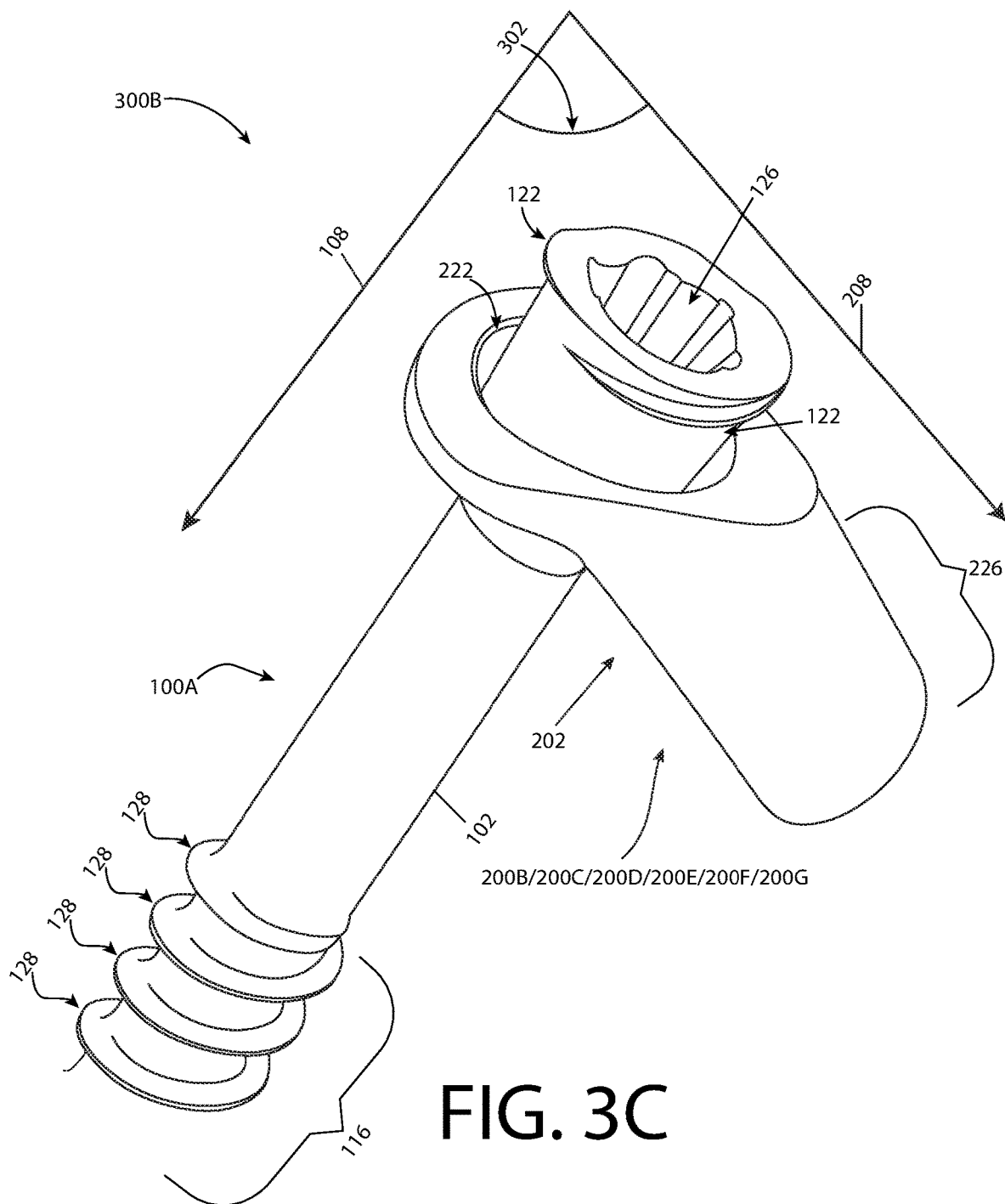
Figure 3D:
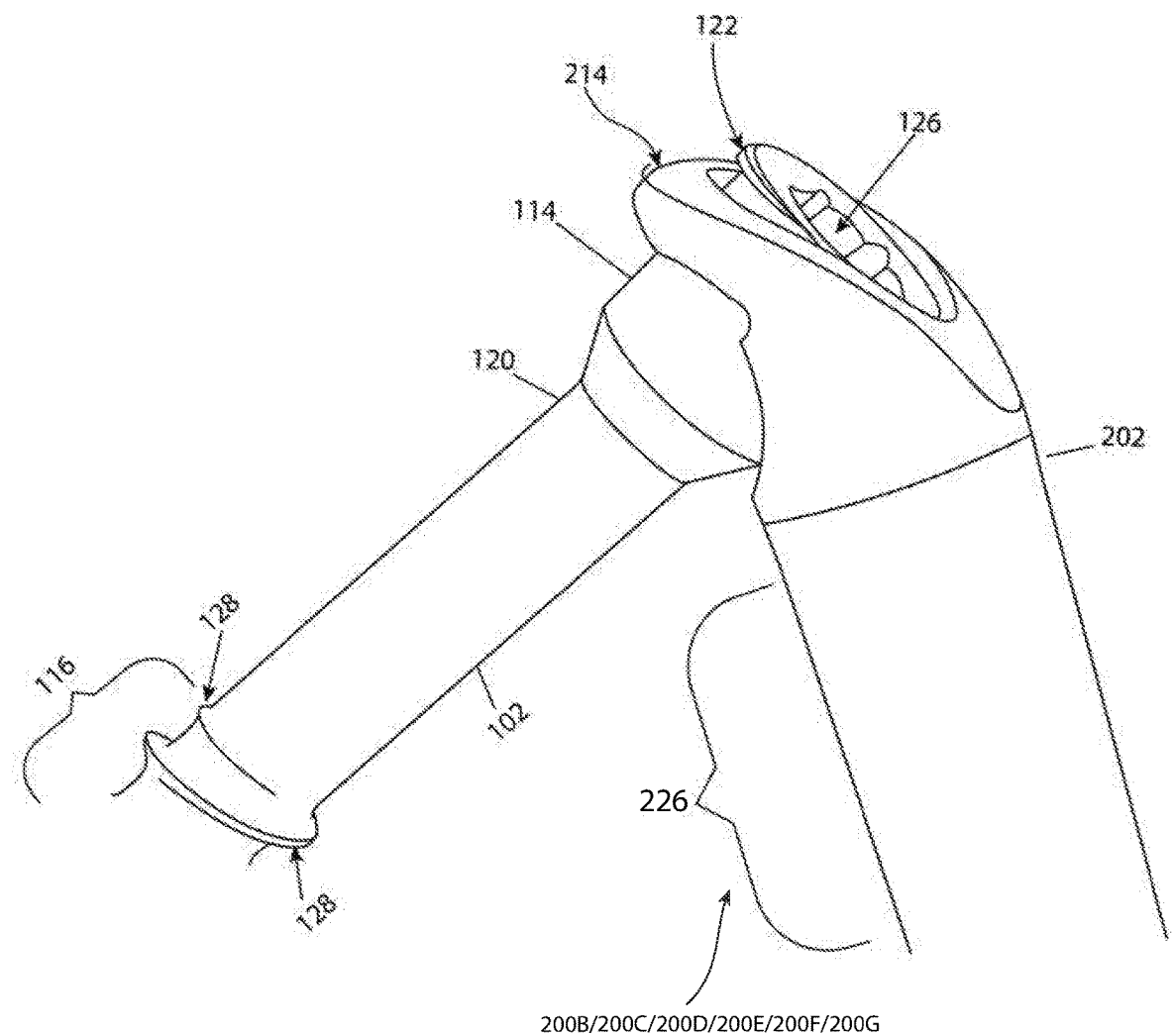

Referring to FIGS. 3C and 3D, FIGS. 3C and 3D illustrate an anteroposterior view and a lateral view, respectively, of an example implant assembly 300B in accordance with various embodiments. As shown, implant assembly 300B can comprise implant device 100A and implant device 200B, 200C, 200D, 200E, 200F, or 200G.

In the various embodiments, the implant device 200B, 200C, 200D, 200E, 200F, or 200G is implanted or inserted (via the nail portion 226) into a bone by striking (e.g., tapping, driving, hammering, nailing, pounding, and/or otherwise similarly inserted) the looped portion 214 to drive the tip and at least a portion of the nail portion 226 into the bone. Implant device 100A is placed and/or inserted through aperture 215 defined by looped portion 214 of the implant device 200B, 200C, 200D, 200E, 200F, or 200G and then implanted/inserted into the same bone and/or a different bone as the implant device 200B, 200C, 200D, 200E, 200F, or 200G. The implant device 100A is implanted or screwed (via one or more threads 128 in the screw portion 116) into the bone while a portion of implant device 100A is inserted through aperture 215 by applying a rotational force to the mechanism 126.

The implant device 100A and the implant device 200B, 200C, 200D, 200E, 200F, or 200G may be engaged with one another by engaging the single thread 122 on the exterior surface of the bulbous portion 114 of implant device 100A with a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G). That is, the rotational force can be applied to the mechanism 126 until the bulbous portion 114 and the looped portion 214 are secured (e.g., tightly secured) and/or abut one another via the single thread 122 and the single groove 222, the plurality of grooves 230, or the substantially smooth or smooth interior surface 232. Further, the implant assembly 300B may be utilized similar to the implant assembly 300A, as discussed elsewhere herein.

Figure 3E:
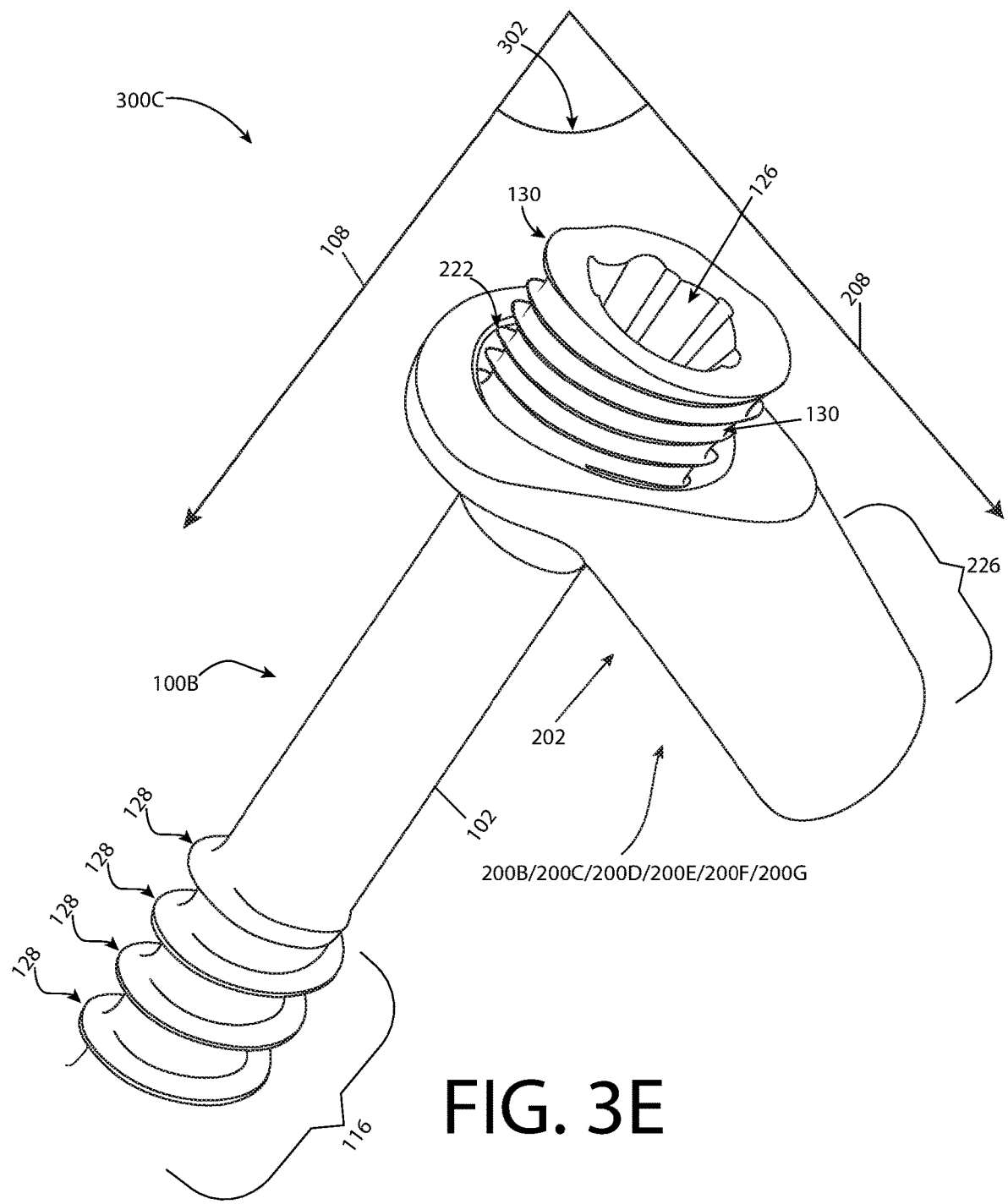
Figure 3F:
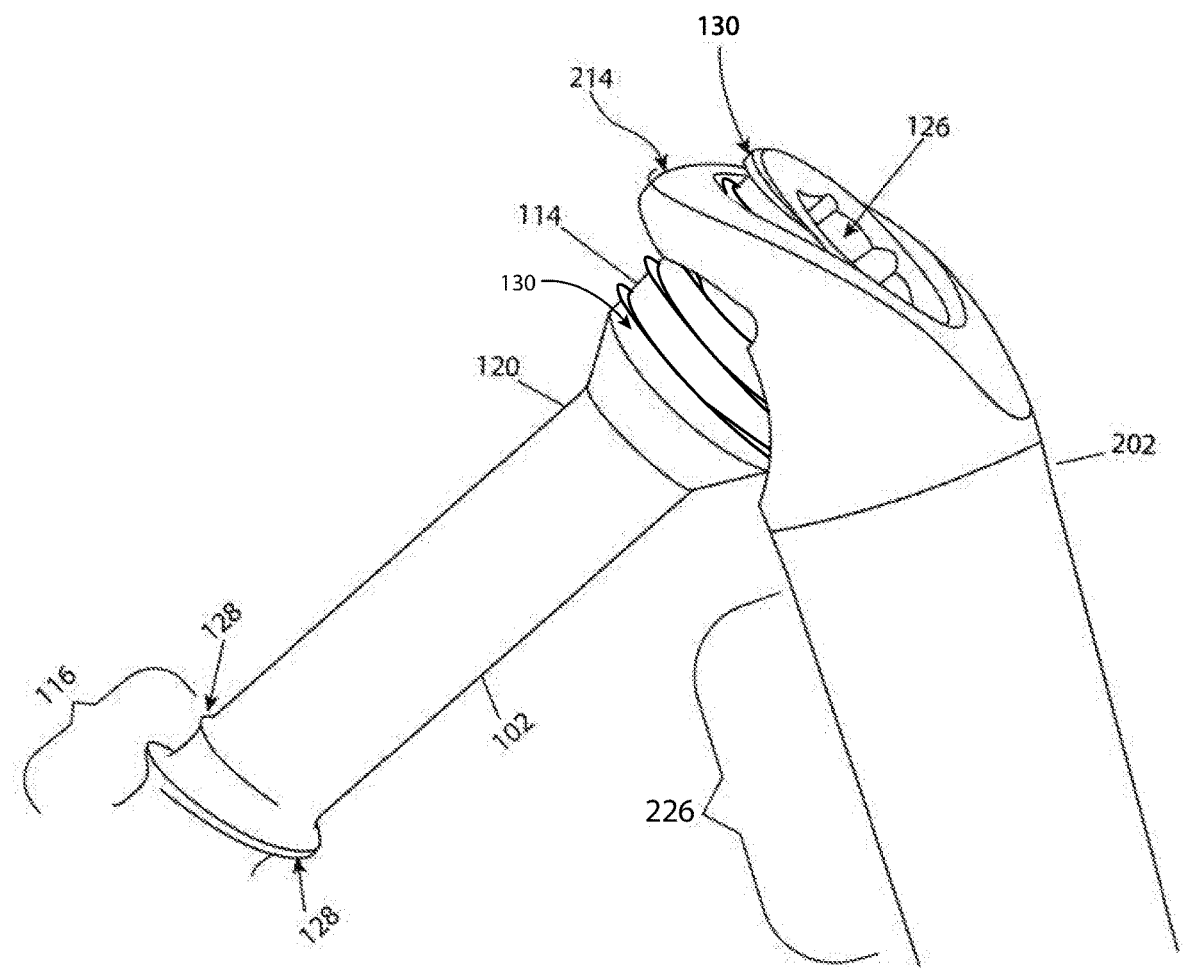

With reference to FIGS. 3E and 3F, FIGS. 3E and 3F illustrate an anteroposterior view and a lateral view, respectively, of an example implant assembly 300C in accordance with various embodiments. As shown, implant assembly 300C can comprise implant device 100B and implant device 200B, 200C, 200D, 200E, 200F, or 200G.

In the various embodiments, the implant device 200B, 200C, 200D, 200E, 200F, or 200G is implanted or inserted (via the nail portion 226) into a bone by striking (e.g., tapping, driving, hammering, nailing, pounding, and/or otherwise similarly inserted) the looped portion 214 to drive the tip and at least a portion of the nail portion 226 into the bone. Implant device 100B is placed and/or inserted through aperture 215 defined by looped portion 214 of the implant device 200B, 200C, 200D, 200E, 200F, or 200G and then implanted/inserted into the same bone and/or a different bone as the implant device 200B, 200C, 200D, 200E, 200F, or 200G. The implant device 100B is implanted or screwed (via one or more threads 128 in the screw portion 116) into the bone while a portion of implant device 100B is inserted through aperture 215 by applying a rotational force to the mechanism 126.

The implant device 100B and the implant device 200B, 200C, 200D, 200E, 200F, or 200G may be engaged with one another by engaging the plurality of thread 130 on the exterior surface of the bulbous portion 114 of implant device 100B with a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G). That is, the rotational force can be applied to the mechanism 126 until the bulbous portion 114 and the looped portion 214 are secured (e.g., tightly secured) and/or abut one another via the plurality of threads 130 and the single groove 222, the plurality of grooves 230, or the substantially smooth or smooth interior surface 232. Further, the implant assembly 300C may be utilized similar to the implant assembly 300A, as discussed elsewhere herein.

Figure 3G:
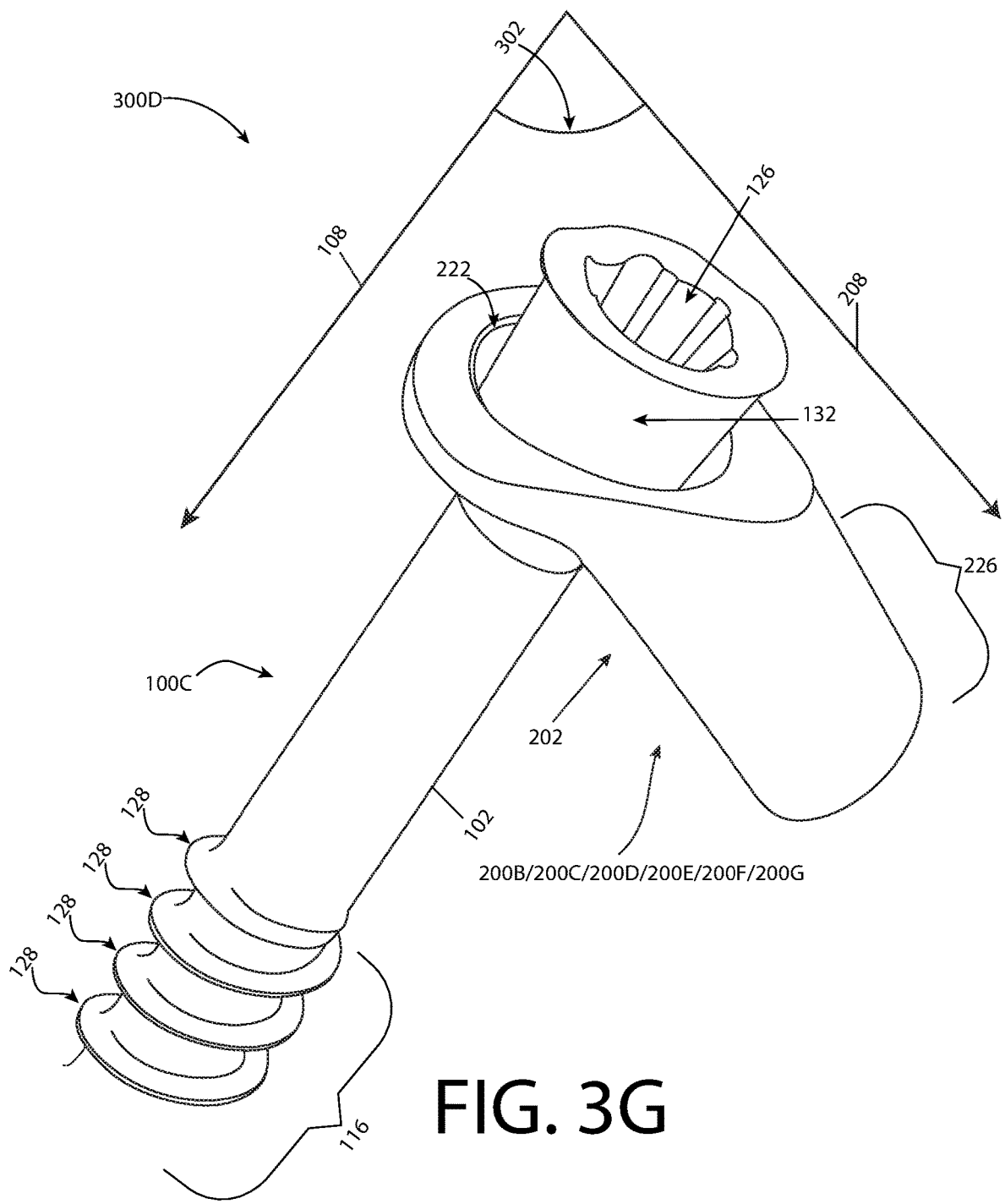
Figure 3H:
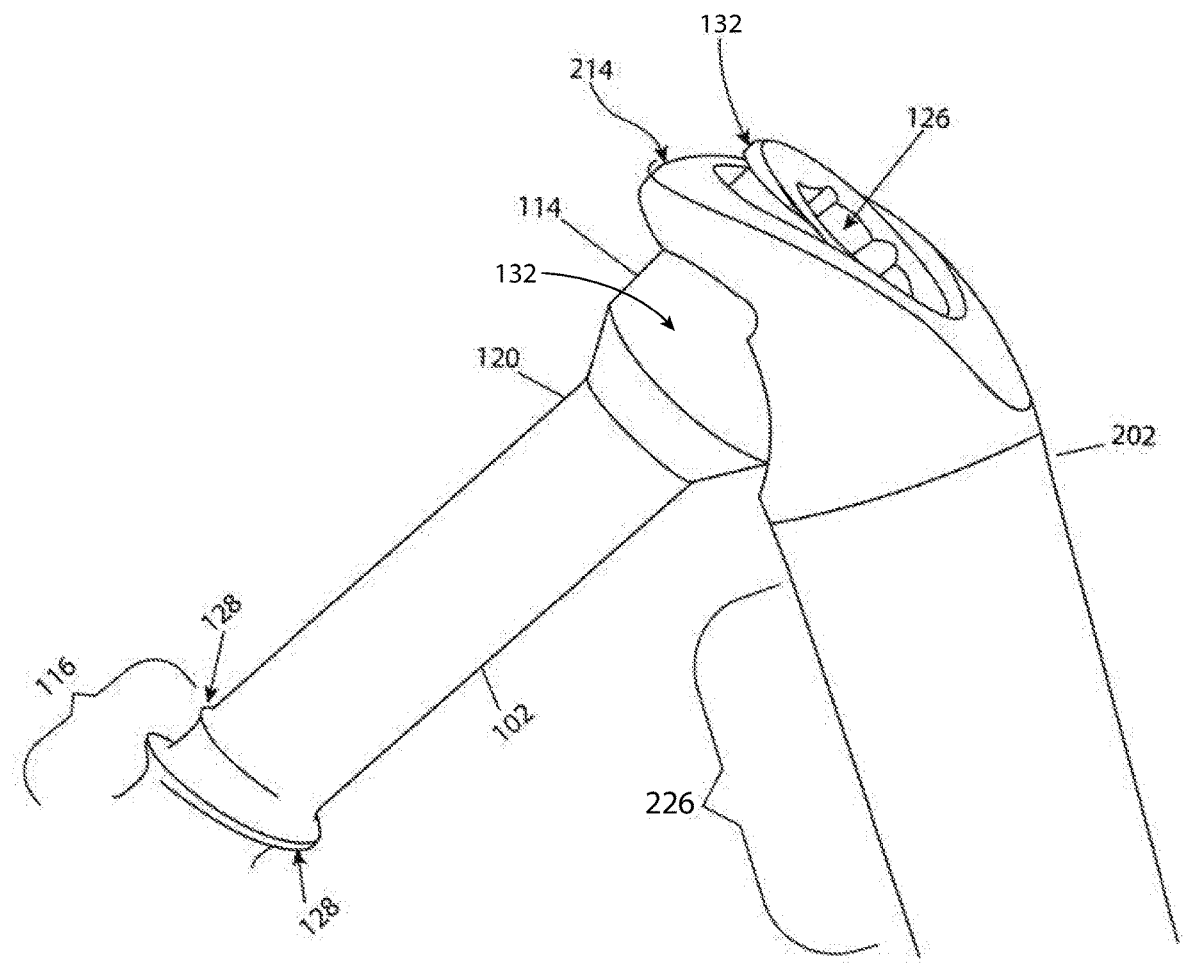

Referring to FIGS. 3G and 3H, FIGS. 3G and 3H illustrate an anteroposterior view and a lateral view, respectively, of an example implant assembly 300D in accordance with various embodiments. As shown, implant assembly 300D can comprise implant device 100C and implant device 200B, 200C, 200D, 200E, 200F, or 200G.

In the various embodiments, the implant device 200B, 200C, 200D, 200E, 200F, or 200G is implanted or inserted (via the nail portion 226) into a bone by striking (e.g., tapping, driving, hammering, nailing, pounding, and/or otherwise similarly inserted) the looped portion 214 to drive the tip and at least a portion of the nail portion 226 into the bone. Implant device 100C is placed and/or inserted through aperture 215 defined by looped portion 214 of the implant device 200B, 200C, 200D, 200E, 200F, or 200G and then implanted/inserted into the same bone and/or a different bone as the implant device 200B, 200C, 200D, 200E, 200F, or 200G. The implant device 100C is implanted or screwed (via one or more threads 128 in the screw portion 116) into the bone while a portion of implant device 100C is inserted through aperture 215 by applying a rotational force to the mechanism 126.

The implant device 100C and the implant device 200B, 200C, 200D, 200E, 200F, or 200G may be engaged with one another by engaging the substantially smooth or smooth exterior surface of the bulbous portion 114 of implant device 100C with a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G). That is, the rotational force can be applied to the mechanism 126 until the bulbous portion 114 and the looped portion 214 are secured (e.g., tightly secured) and/or abut one another via the smooth/substantially smooth bulbous portion 114 and the single groove 222, the plurality of grooves 230, or the substantially smooth or smooth interior surface 232. Further, the implant assembly 300D may be utilized similar to the implant assembly 300A, as discussed elsewhere herein.

Figure 4:
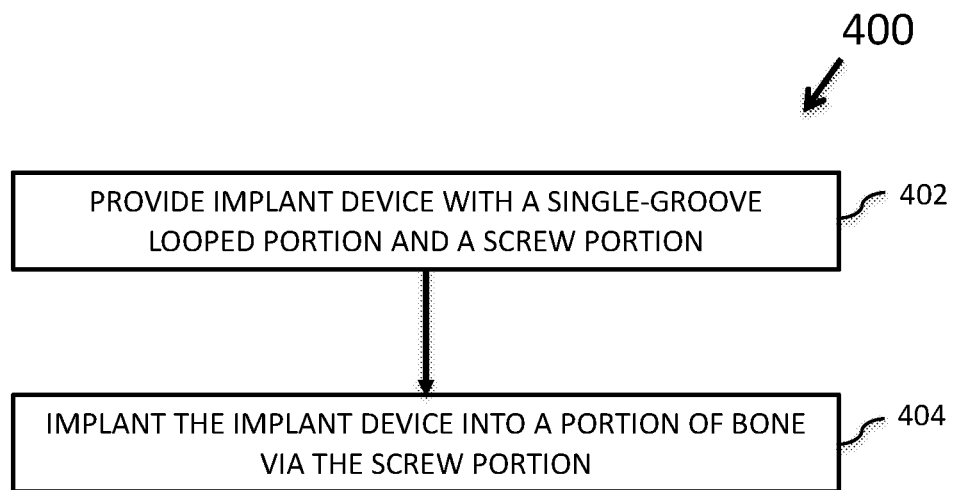
FIG. 4 is a schematic diagram illustrating one embodiment of a method for implanting the implant device of FIG. 2A.

With reference to FIG. 4, FIG. 4 is a schematic diagram illustrating one embodiment of a method 400 for implanting implant device 200A. At least in the illustrated embodiment, method 400 begins by providing an implant device 200A that includes a looped portion 214 and a screw portion 216 (block 402).

The method 400 further includes implanting the implant device 200A into a portion of bone via the screw portion 216 (block 404). The implant device 200A may be implanted by applying a rotational force to the looped portion 214 of the implant device 200A until the screw portion 216 is securely engaged, embedded, and/or implanted into the bone, as discussed elsewhere herein.

Figure 5:
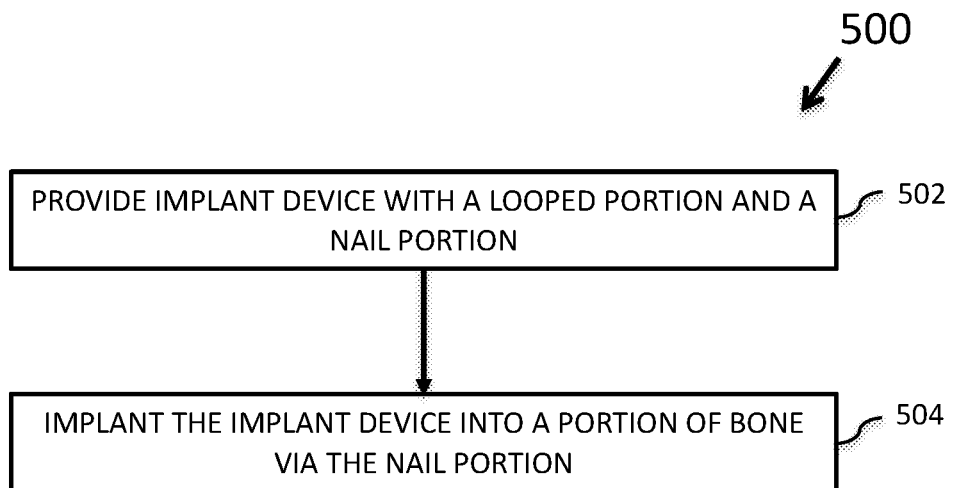
FIG. 5 is a schematic diagram illustrating one embodiment of a method for implanting the implant devices of FIGS. 2B through 2G.

Referring to FIG. 5, FIG. 5 is a schematic diagram illustrating one embodiment of a method 500 for implanting an implant device 200B, 200C, 200D, 200E, 200F, or 200G. At least in the illustrated embodiment, method 500 begins by providing an implant device 200B, 200C, 200D, 200E, 200F, or 200G that includes a looped portion 214 and a nail portion 226 (block 502).

The method 500 further includes implanting the implant device 200B, 200C, 200D, 200E, 200F, or 200G into a portion of bone via the nail portion 226 (block 504). The implant device 200B, 200C, 200D, 200E, 200F, or 200G may be implanted by striking the looped portion 214 of the implant device 200B, 200C, 200D, 200E, 200F, or 200G until a tip and at least a portion of the nail portion 226 is securely engaged, embedded, and/or implanted into the bone, as discussed elsewhere herein.

Figure 6:
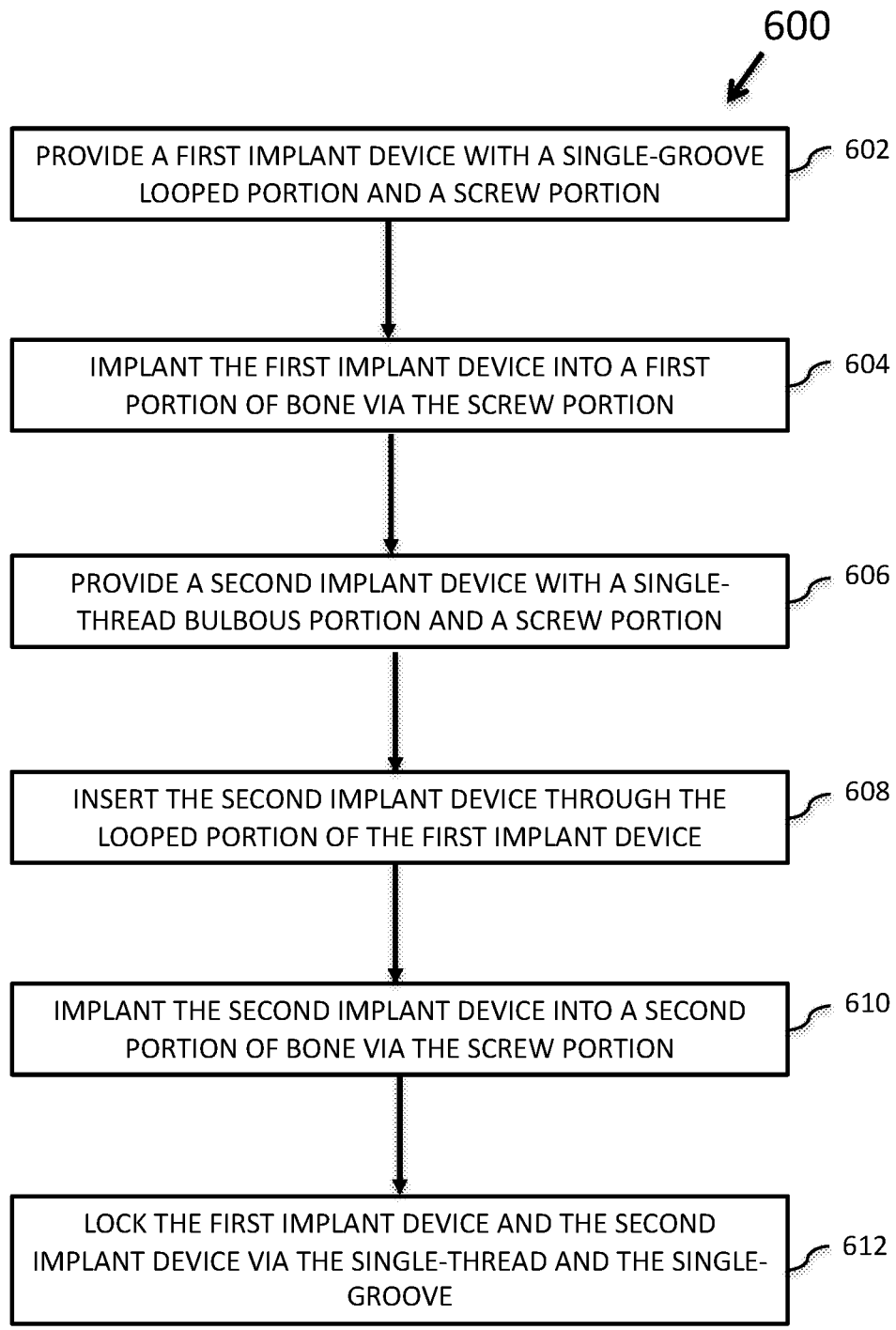
FIG. 6 is a schematic diagram illustrating one embodiment of a method for compressing a set of bones utilizing the implant assembly of FIGS. 3A and 3B.

With reference to FIG. 6, FIG. 6 is a schematic diagram illustrating one embodiment of a method 600 for compressing a set of bones utilizing an implant assembly 300A. At least in the illustrated embodiment, method 600 begins by providing an implant device 200A that includes a looped portion 214 and a screw portion 216 (block 602).

The implant device 200A is then implanted into a first portion of bone via the screw portion 216 (block 604). The implant device 200A may be implanted by applying a rotational force to the looped portion 214 of the implant device 200A until the screw portion 216 is securely engaged, embedded, and/or implanted into the bone, as discussed elsewhere herein.

Method 600 further includes providing an implant device 100A that includes a bulbous portion 114 and a screw portion 116 (block 606). The implant device 100A is inserted through the looped portion of the implant device 200A (block 608) and implanted into a second portion of bone (block 610), which can be the same bone or different bone as implant device 200A.

The implant devices 100A and 200A are locked and/or engaged with one another via the single thread 122 on the exterior surface of the bulbous portion 114 and the single groove 222 on the interior surface of the looped portion 214 (block 612). In various embodiments, implant devices 100A and 200A are locked and/or engaged with one another by applying a rotational force to the mechanism 126 on the implant device 100A until the screw portion 116 is securely engaged, embedded, and/or implanted into the bone and the single thread 122 and the single groove 222 are secured to one another, as discussed elsewhere herein. When engaged, the implant devices 100A and 200A can provide a force and/or compression to the set of bones (e.g., one or more bones) into which the implant devices 100A and 200A are implanted to assist in healing and/or repairing the bone(s).

In some embodiments, locking the implant devices 100A and 200A includes facilitating locking the implant devices 100A and 200A. Here, facilitating locking the implant devices 100A and 200A can include providing tools, instructions, and/or other means for locking the implant devices 100A and 200A. In other embodiments, locking the implant devices 100A and 200A includes both facilitating locking the implant devices 100A and 200A and actually locking the implant devices 100A and 200A, as discussed above.

Figure 7:
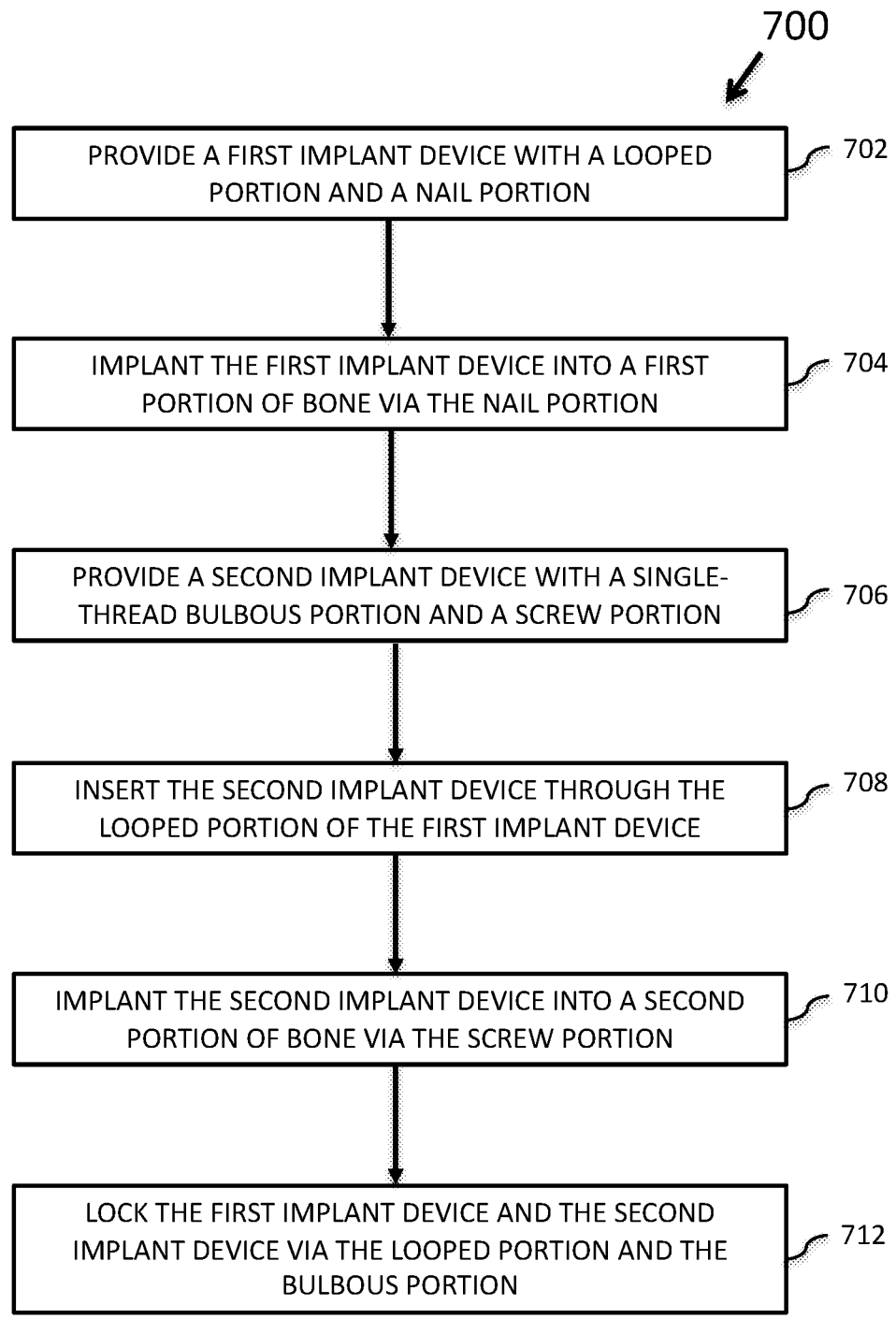
FIG. 7 is a schematic diagram illustrating one embodiment of another method for compressing a set of bones utilizing the implant assembly of FIGS. 3C and 3D.

Referring to FIG. 7, FIG. 7 is a schematic diagram illustrating one embodiment of a method 700 for compressing a set of bones utilizing an implant assembly 300B. At least in the illustrated embodiment, method 700 begins by providing an implant device 200B, 200C, 200D, 200E, 200F, or 200G that includes a looped portion 214 and a nail portion 226 (block 702).

The implant device 200B, 200C, 200D, 200E, 200F, or 200G is then implanted into a first portion of bone via the nail portion 226 (block 704). The implant device 200B, 200C, 200D, 200E, 200F, or 200G may be implanted by striking the looped portion 214 of the implant device 200B, 200C, 200D, 200E, 200F, or 200G until a tip and at least a portion of the nail portion 226 is securely engaged, embedded, and/or implanted into the first portion of bone, as discussed elsewhere herein.

Method 700 further includes providing an implant device 100A that includes a bulbous portion 114 and a screw portion 116 (block 706). The implant device 100A is inserted through the looped portion of the implant device 200B, 200C, 200D, 200E, 200F, or 200G (block 708) and implanted into a second portion of bone (block 710), which can be the same bone or different bone as implant device 200B, 200C, 200D, 200E, 200F, or 200G.

The implant device 100A and implant device 200B, 200C, 200D, 200E, 200F, or 200G are locked and/or engaged with one another via the single thread 122 on the exterior surface of the bulbous portion 114 and a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G) (block 712). That is, the rotational force can be applied to the mechanism 126 until the bulbous portion 114 and the looped portion 214 are secured (e.g., tightly secured) and/or abut one another via the single groove 122 and the single groove 222, the plurality of grooves 230, or the substantially smooth or smooth interior surface 232.

In various embodiments, implant device 100A and implant device 200B, 200C, 200D, 200E, 200F, or 200G are locked and/or engaged with one another by applying a rotational force to the mechanism 126 on the implant device 100A until the screw portion 116 is securely engaged, embedded, and/or implanted into the bone and the single thread 122 and the single groove 222, the plurality of grooves 230 or the smooth/substantially smooth interior surface 232 of the looped portion 214 are secured to one another, as discussed elsewhere herein. When engaged, the implant device 100A and implant device 200B, 200C, 200D, 200E, 200F, or 200G can provide a force and/or compression to the set of bones (e.g., one or more bones) into which the implant device 100A and implant device 200B, 200C, 200D, 200E, 200F, or 200G are implanted to assist in healing and/or repairing the bone(s).

In some embodiments, locking the implant device 100A and implant device 200B, 200C, 200D, 200E, 200F, or 200G includes facilitating locking the implant device 100A and implant device 200B, 200C, 200D, 200E, 200F, or 200G. Here, facilitating locking the implant device 100A and implant device 200B, 200C, 200D, 200E, 200F, or 200G can include providing tools, instructions, and/or other means for locking the implant device 100A and implant device 200B, 200C, 200D, 200E, 200F, or 200G. In other embodiments, locking the implant device 100A and implant device 200B, 200C, 200D, 200E, 200F, or 200G includes both facilitating locking the implant device 100A and implant device 200B, 200C, 200D, 200E, 200F, or 200G and actually locking the implant device 100A and implant device 200B, 200C, 200D, 200E, 200F, or 200G, as discussed above.

Figure 8:
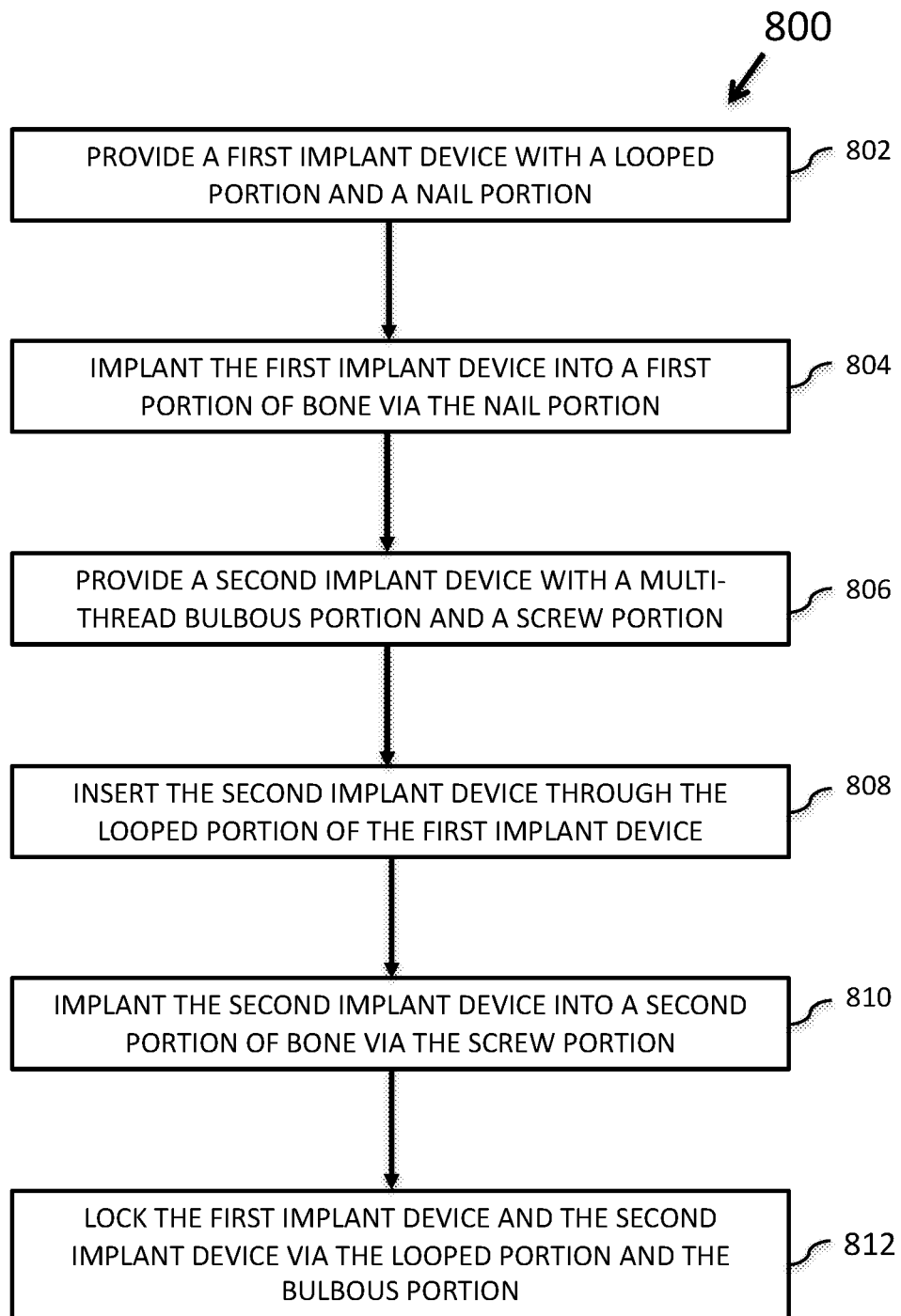
FIG. 8 is a schematic diagram illustrating one embodiment of yet another method for compressing a set of bones utilizing the implant assembly of FIGS. 3E and 3F.

Referring to FIG. 8, FIG. 8 is a schematic diagram illustrating one embodiment of a method 800 for compressing a set of bones utilizing an implant assembly 300C. At least in the illustrated embodiment, method 800 begins by providing an implant device 200B, 200C, 200D, 200E, 200F, or 200G that includes a looped portion 214 and a nail portion 226 (block 802).

The implant device 200B, 200C, 200D, 200E, 200F, or 200G is then implanted into a first portion of bone via the nail portion 226 (block 804). The implant device 200B, 200C, 200D, 200E, 200F, or 200G may be implanted by striking the looped portion 214 of the implant device 200B, 200C, 200D, 200E, 200F, or 200G until a tip and at least a portion of the nail portion 226 is securely engaged, embedded, and/or implanted into the first portion of bone, as discussed elsewhere herein.

Method 800 further includes providing an implant device 100B that includes a bulbous portion 114 and a screw portion 116 (block 806). The implant device 100B is inserted through the looped portion of the implant device 200B, 200C, 200D, 200E, 200F, or 200G (block 808) and implanted into a second portion of bone (block 810), which can be the same bone or different bone as implant device 200B, 200C, 200D, 200E, 200F, or 200G.

The implant device 100B and implant device 200B, 200C, 200D, 200E, 200F, or 200G are locked and/or engaged with one another via the plurality of threads 130 on the exterior surface of the bulbous portion 114 and a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G) (block 812). That is, the rotational force can be applied to the mechanism 126 until the bulbous portion 114 and the looped portion 214 are secured (e.g., tightly secured) and/or abut one another via the plurality of grooves 130 and the single groove 222, the plurality of grooves 230, or the substantially smooth or smooth interior surface 232.

In various embodiments, implant device 100B and implant device 200B, 200C, 200D, 200E, 200F, or 200G are locked and/or engaged with one another by applying a rotational force to the mechanism 126 on the implant device 100B until the screw portion 116 is securely engaged, embedded, and/or implanted into the bone and the plurality of threads 130 and the single groove 222, the plurality of grooves 230 or the smooth/substantially smooth interior surface 232 of the looped portion 214 are secured to one another, as discussed elsewhere herein. When engaged, the implant device 100B and implant device 200B, 200C, 200D, 200E, 200F, or 200G can provide a force and/or compression to the set of bones (e.g., one or more bones) into which the implant device 100B and implant device 200B, 200C, 200D, 200E, 200F, or 200G are implanted to assist in healing and/or repairing the bone(s).

In some embodiments, locking the implant device 100B and implant device 200B, 200C, 200D, 200E, 200F, or 200G includes facilitating locking the implant device 100B and implant device 200B, 200C, 200D, 200E, 200F, or 200G. Here, facilitating locking the implant device 100B and implant device 200B, 200C, 200D, 200E, 200F, or 200G can include providing tools, instructions, and/or other means for locking the implant device 100B and implant device 200B, 200C, 200D, 200E, 200F, or 200G. In other embodiments, locking the implant device 100B and implant device 200B, 200C, 200D, 200E, 200F, or 200G includes both facilitating locking the implant device 100B and implant device 200B, 200C, 200D, 200E, 200F, or 200G and actually locking the implant device 100B and implant device 200B, 200C, 200D, 200E, 200F, or 200G, as discussed above.

Figure 9:
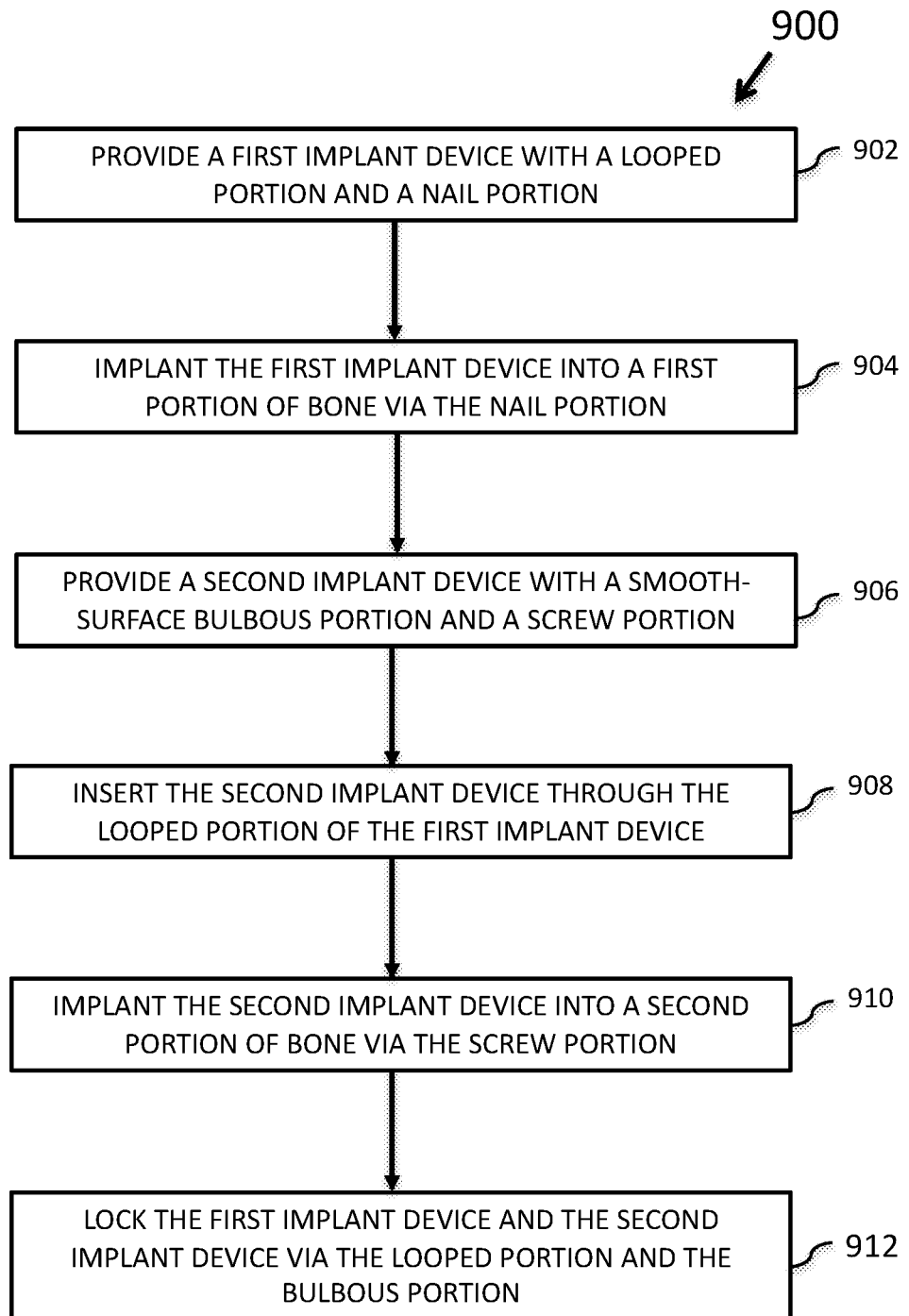
FIG. 9 is a schematic diagram illustrating one embodiment of still another method for compressing a set of bones utilizing the implant assembly of FIGS. 3G and 3H.

With reference to FIG. 9, FIG. 9 is a schematic diagram illustrating one embodiment of a method 900 for compressing a set of bones utilizing an implant assembly 300D. At least in the illustrated embodiment, method 900 begins by providing an implant device 200B, 200C, 200D, 200E, 200F, or 200G that includes a looped portion 214 and a nail portion 226 (block 902).

The implant device 200B, 200C, 200D, 200E, 200F, or 200G is then implanted into a first portion of bone via the nail portion 226 (block 904). The implant device 200B, 200C, 200D, 200E, 200F, or 200G may be implanted by striking the looped portion 214 of the implant device 200B, 200C, 200D, 200E, 200F, or 200G until a tip and at least a portion of the nail portion 226 is securely engaged, embedded, and/or implanted into the first portion of bone, as discussed elsewhere herein.

Method 900 further includes providing an implant device 100C that includes a bulbous portion 114 and a screw portion 116 (block 906). The implant device 100C is inserted through the looped portion of the implant device 200B, 200C, 200D, 200E, 200F, or 200G (block 908) and implanted into a second portion of bone (block 910), which can be the same bone or different bone as implant device 200B, 200C, 200D, 200E, 200F, or 200G.

The implant device 100C and implant device 200B, 200C, 200D, 200E, 200F, or 200G are locked and/or engaged with one another via the smooth/substantially smooth exterior surface 132 of the bulbous portion 114 and a single groove 222 on the interior surface of the looped portion 214 (e.g., implant devices 200B and 200C), a plurality of grooves 230 on the interior surface of the looped portion 214 (e.g., implant devices 200D and 200E), or a substantially smooth or smooth interior surface 232 of the looped portion 214 (e.g., implant devices 200F and 200G) (block 912). That is, the rotational force can be applied to the mechanism 126 until the bulbous portion 114 and the looped portion 214 are secured (e.g., tightly secured) and/or abut one another via the smooth/substantially smooth interior surface 232 and the single groove 222, the plurality of grooves 230, or the substantially smooth or smooth interior surface 232.

In various embodiments, implant device 100C and implant device 200B, 200C, 200D, 200E, 200F, or 200G are locked and/or engaged with one another by applying a rotational force to the mechanism 126 on the implant device 100C until the screw portion 116 is securely engaged, embedded, and/or implanted into the bone and the smooth/substantially smooth exterior surface 132 of the bulbous portion 114 and the single groove 222, the plurality of grooves 230 or the smooth/substantially smooth interior surface 232 of the looped portion 214 are secured to one another, as discussed elsewhere herein. When engaged, the implant device 100C and implant device 200B, 200C, 200D, 200E, 200F, or 200G can provide a force and/or compression to the set of bones (e.g., one or more bones) into which the implant device 100B and implant device 200B, 200C, 200D, 200E, 200F, or 200G are implanted to assist in healing and/or repairing the bone(s).

In some embodiments, locking the implant device 100C and implant device 200B, 200C, 200D, 200E, 200F, or 200G includes facilitating locking the implant device 100C and implant device 200B, 200C, 200D, 200E, 200F, or 200G. Here, facilitating locking the implant device 100C and implant device 200B, 200C, 200D, 200E, 200F, or 200G can include providing tools, instructions, and/or other means for locking the implant device 100C and implant device 200B, 200C, 200D, 200E, 200F, or 200G. In other embodiments, locking the implant device 100C and implant device 200B, 200C, 200D, 200E, 200F, or 200G includes both facilitating locking the implant device 100C and implant device 200B, 200C, 200D, 200E, 200F, or 200G and actually locking the implant device 100C and implant device 200B, 200C, 200D, 200E, 200F, or 200G, as discussed above.

The embodiments may be practiced in other specific forms. The described embodiments are to be considered in all respects only as illustrative and not restrictive. The scope of the technology is, therefore, indicated by the appended claims rather than by the foregoing description. All changes which come within the meaning and range of equivalency of the claims are to be embraced within their scope.

The invention claimed is:

1. A method, comprising: providing a first implant device, the first implant device comprising: a first end and a second end oppositely located along a longitudinal first axis, a looped portion including an aperture and defining a first terminal axis at the first end, and a nail portion that extends along the longitudinal first axis and defining a second terminal axis at the second end, the nail portion comprising a hole extending transversely along an axis, and including a smooth interior surface located proximate to the fourth end, wherein said hole has a uniform diameter along said axis; providing a second implant device, the second implant device comprising: a third end and a fourth end oppositely located along a longitudinal second axis, a bulbous portion that extends along the longitudinal second axis and defines a third terminal axis at the third end, and a threaded portion that extends along the longitudinal second axis and defines a fourth terminal axis at the fourth end; and one of: facilitating locking the first implant device and the second implant device, locking the first implant device and the second implant device, and both facilitating locking the first implant device and the second implant device and locking the first implant device and the second implant device.

2. The method of claim 1, wherein:
the first implant device and the second implant device are locked; and
the method further comprises implanting the first implant device into a first portion of bone prior to locking the first implant device and the second implant device.

3. The method of claim 2, wherein:
implanting the first implant device comprises striking the looped portion of the first implant device to drive the nail portion into the first portion of bone.

4. The method of claim 2, further comprising:
inserting the second implant device through the aperture of the looped portion subsequent to implanting the first implant device and prior to locking the first implant device and the second implant device.

5. The method of claim 4, further comprising:
implanting the second implant device into a second portion of bone while the second implant device is inserted through the aperture of the looped portion,
wherein:
the first portion of bone and the second portion of bone are one of located on different bones and located on a common bone.

6. The method of claim 5, wherein:
implanting the first implant device comprises:
presenting the nail portion at the first portion of bone, and
striking the looped portion of the first implant device to drive the nail portion into the first portion of bone; and
implanting the second implant device comprises:
presenting the threaded portion at the second portion of bone while the second implant device is inserted through the aperture of the looped portion, and
applying, at the bulbous portion, a rotational force around the longitudinal second axis.

7. The method of claim 1, wherein:
the looped portion comprises a first shape;
the bulbous portion comprises a second shape; and
the first shape of the looped portion corresponds to the second shape of the bulbous portion.

8. The method of claim 7, wherein the first shape allows the first implant device to be inserted through the looped portion.

9. The method of claim 7, wherein the first shape comprises a circular shape.

10. A method, comprising:
providing an implant device, the implant device comprising:
a first end and a second end oppositely located along a longitudinal first axis,
a looped portion including an aperture and defining a first terminal axis at the first end, and
a nail portion that extends along the longitudinal first axis and defining a second
terminal axis at the second end, the nail portion comprising a hole extending transversely along a second axis, and including a smooth interior surface located proximate to the fourth end, wherein said hole has a uniform diameter along said second axis; and implanting the implant device into a portion of bone via the nail portion.

11. The method of claim 10, wherein the nail portion comprises:
a tip; and
a smooth portion or a substantially smooth portion.

12. The method of claim 11, wherein implanting the implant device via the nail portion comprises:
striking the looped portion of the implant device to drive the tip and at least part of the smooth portion or the substantially smooth portion into the portion of bone.

13. The method of claim 10, wherein implanting the implant device via the nail portion comprises:
striking the looped portion of the implant device to drive the nail portion into the portion of bone.

14. The method of claim 10, wherein:
the looped portion comprises a first shape;
the bulbous portion comprises a second shape; and
the first shape of the looped portion corresponds to the second shape of the bulbous portion.

15. The method of claim 14, wherein the first shape allows the first implant device to be inserted through the looped portion.

16. The method of claim 14, wherein the first shape comprises a circular shape.

\* \* \* \* \*